United States Patent [19]
John et al.

[11] Patent Number: 5,919,934
[45] Date of Patent: Jul. 6, 1999

[54] COMPOUNDS, COMPOSITIONS, AND METHODS FOR CANCER IMAGING AND THERAPY

[75] Inventors: Christy Seith John, Gaithersburg; Benjamin Byung-Duk Lim, Sykesville, both of Md.

[73] Assignee: The George Washington University, Washington, D.C.

[21] Appl. No.: 08/802,275

[22] Filed: Feb. 19, 1997

[51] Int. Cl.$^6$ ........................ C07D 211/32; C07D 211/56; C07F 13/00

[52] U.S. Cl. ..................... 546/247; 546/246; 540/610; 548/567; 564/511; 564/512; 534/10; 534/14

[58] Field of Search .................... 540/610; 546/246; 546/247; 548/567; 564/511, 512; 534/10, 14

[56] References Cited

U.S. PATENT DOCUMENTS

| | | | |
|---|---|---|---|
| 4,584,187 | 4/1986 | Wieland et al. | 424/1.1 |
| 4,925,650 | 5/1990 | Nosco et al. | 424/1.1 |
| 5,122,361 | 6/1992 | Kung et al. | 424/1.1 |
| 5,154,913 | 10/1992 | de Paulis et al. | 424/1.1 |
| 5,190,741 | 3/1993 | Moreau et al. | 424/1.1 |
| 5,262,175 | 11/1993 | Solanki | 424/1.1 |
| 5,387,614 | 2/1995 | Schoenwald et al. | 514/654 |
| 5,457,207 | 10/1995 | Efange et al. | 546/17 |
| 5,498,618 | 3/1996 | Leysen et al. | 514/329 |
| 5,499,761 | 3/1996 | Belinka | 534/10 |
| 5,679,778 | 10/1997 | Abrams et al. | 530/391.5 |
| 5,688,487 | 11/1997 | Linder . | |

FOREIGN PATENT DOCUMENTS

WO 94/26314  11/1994  WIPO .

OTHER PUBLICATIONS

Walker "Sigma Receptors . . . " PHar. Rev. v.42, p. 355, 378–380, relevant pages only, 1990.

Rubini et al. "synthesis of isosteric methylene–oxy pseudo-dipeptide . . . " Tetrahedron v.42 pp. 6039–6045, 1986.

Hamada et al., Translational and rotational diffusion of spin probes in nylon films, Chemical Abstracts, vol. 107(12): 97482x (1987).

Shigemitsu et al., Nonlinear optical devices, Chemical Abstracts, vol. 116(16): 162155v (1992).

Hom, et al., "Heterodimeric Bis(amino thiol) Complexes of Oxorhenium(V) That Mimic the Structure of Steroid Hormones. Synthesis and Sterochemical Issues," *J. Org. Chem.*, 61:2624–2631 (1996).

George, et al., "Radiometal labeling of recombinant proteins by a genetically engineered minimal chelation site: Technetium–99m coordination by single–chain Fv antibody fusion proteins through a C–terminal cysteinyl peptide," *Proc. Natl. Acad. Sci. USA*, 92:8358–8362 (1995).

Meegalla, et al., "First Example of a $^{99m}$Tc Complex as a Dopamine Transporter Imaging Agent," *J. Am Chem Soc.*, 117:11037–11038 (1995).

Vanbilloen, et al., "Complexes of Technetium–99m with Tetrapeptides, a New Class of $^{99m}$Tc–labelled Agents," *Nucl. Med. Biol.*, 22:325–338 (1995).

Oya, et al., "New Bisaminoethanethiol (BAT) Ligands Which Form Two Interconvertible Tc–99m Complexes," *Nucl. Med. Biol.*, 22:749–757 (1995).

Lever, et al., "Novel Technetium Ligands with Affinity for the Muscarinic Cholinergic Receptor," *Nucl. Med. Biol.*, 21:157–164 (1994).

Chi, et al., "Homodimeric and Heterodimeric Bis(amino thiol) Oxometal Complexes with Rhenium(V) and Technetium(V). Control of Heterodimeric Complex Formation and an Approach to Metal Complexes that Mimic Steriod Hormones," *J. Med. Chem.* 37:928–937 (1994).

O'Neil, et al., "Progestin Radiopharmaceuticals Labeled with Technetium and Rhenium: Synthesis, Binding Affinity, and in Vivo Distribution of a New Progestin $N_2S_2$—Metal Conjugate," *Bioconjugate Chem.*, 5:182–193 (1994).

Bormans, et al., "Investigation of the Labelling Characteristics of $^{99m}$Tc–Mercaptoacetyltriglycine," *Nucl. Med. Biol.*, 3:339–349 (1995).

Del Rosario, et al., "Synthesis and In Vivo Evaluation of a $^{99m/99}$Tc–DADT–Benzovesamicol: a Potential Marker for Cholinergic Neurons," *Nucl. Med. Biol.*, 21:197–203 (1994).

John, et al., "Synthesis and Characterization of Neutral Oxotechnetium(V) Bisaminoethanethol Complexes: Potential Brain Imaging Agents," *Polyhedron*, 11:1145–1155 (1992).

Rao, et al., "Technetium(V) and Rhenium(V) Complexes of 2,3–Bis(mercaptoacetamido)propanoate. Chelate Ring Stereochemistry and Influence on Chemical and Biological Properties," *J. Am. Chem. Soc.*, 112:5798–5804 (1990).

Brandau, et al., "Technetium–99m Labeled Renal Function and Imaging Agents: III. Synthesis of $^{99m}$Tc–MA and Biodistribution of By–products," *Appl. Radiot. Isot.*, 39: 121–129 (1988).

Fritzberg, et al., "Synthesis and Biological Evaluation of Technetium–99m MAG$_3$ as a Hippuran Replacement," *J. Nucl. Med.*, 27:111–116 (1986).

Scheffel, et al., "Comparison of Technetium–99m Aminoalkyl Diaminodithiol (DADT) Analogs as Potential Brain Blood Flow Imaging Agents," *J. Nucl. Med.*, 29:73–82 (1988).

DiZio, et al., "Technetium– and Rhenium–Labeled Progestins: Synthesis, Receptor Binding and In Vivo Distribution of an 11β–Substituted Progestin Labeled with Technetium–99 and Rhenium–186," *J. Nucl. Med.*, 33:558–569 (1992).

(List continued on next page.)

*Primary Examiner*—Ceila Chang
*Attorney, Agent, or Firm*—Finnegan, Henderson, Farabow, Garrett & Dunner, L.L.P.

[57] ABSTRACT

Disclosed are bisaminothiol and amino compounds with appended pharmacophores, complexes of these compounds with $^{99m}$Tc(V)0, Re(V)0, In$^{+3}$, $^{67}$Ga$^{+3}$, $^{90}$Y$^{+3}$, $^{109}$Pd$^{+2}$ or $^{105}$Rh$^{+3}$, and pharmaceutical compositions containing the complexes. Also disclosed are methods of diagnosing a mammal for the presence of a mammalian tumor, methods for in vitro detection of a cancer cell in a mammalian tissue sample, and methods of treating a mammal having a tumor.

45 Claims, 3 Drawing Sheets

OTHER PUBLICATIONS

Lever, et al., "Design, Preparation, and Biodistribution of a Technetium–99m Triaminedithiol Complex to Assess Regional Cerebral Blood Flow," *J. Nucl. Med.*, 26:1287–1294 (1985).

Kasina, et al., "Tissue Distribution Properties of Technetium–99m–Diamide–Dimercaptide Complexes and Potential Use as Renal Radiopharmaceuticals," *J. Med. Chem.*, 29:1933–1940 (1986).

John, et al., "Synthesis, In Vitro Validation and In Vivo Pharmacokinetics of [$^{125}$I]N–[2–(4–Iodopheny)Ethyl]–N–Methyl–2–(1–Piperidinyl) Ethylamine: A High–Affinity Ligand for Imaging Sigma Receptor Positive Tumors," Nucl. Med. Biol., 23:761–766 (1996).

Vilner, et al., "Sigma–1 and Sigma–2 Receptors Are Expressed in a Wide Variety of Human and Rodent Tumor Cell Lines," Cancer Research, 55:408–413 (1995).

John et al., "Synthesis and Characterization of [$^{125}$I]–N–(N–Benzylpiperidin–4–yl)–4–iodobenzamide, a New σ Receptor Radiopharmceutical: High–Affinity Binding to MCF–7 Breast Tumor Cells," Am. Chem. Soc.1737–1739 (1994).

John, et al., "A Malignant Melanoma Imaging Agent: Synthesis, Characterization, In Vitro Binding and Biodistribution of Iodine–125–(2–Piperidinylaminoethyl)4–Iodobenzamide," J. Nucl. Med. 34:2169–2175 (1993).

John, et al., "Sigma Receptors are Expressed in Human Non–Small Cell Lung Carcinoma," Life Sciences, 56:2385–2392 (1995).

John, et al., "Synthesis and Pharmacological Characterization of 4–[$^{125}$I}–N–(N–Benzylpiperidin–4–yl)–4–iodobenzamide: A High Affinity σ Receptor Ligand for Potential Imaging of Breast Cancer," Cancer Research, 55:3022–3027 (1995).

Gore, et al., "Differences in the Hepatic Metabolism of $^{99m}$Tc and $^{125}$I labelled Galactosyl Neoglycoalbumin," J. Am. Chem. Soc., 117:11821–11822 (1995).

COMPOUNDS, COMPOSITIONS, AND METHODS FOR CANCER IMAGING AND THERAPY

FILED OF THE INVENTION:

The present invention relates to compounds and complexes having particular affinity for a specific cell surface receptor prevalent on certain cancer cells. In particular, the present invention provides such compounds as agents for detecting and treating tumors having cancer cells which possess a cell surface sigma receptor.

BACKGROUND OF THE INVENTION:

Lung carcinomas, malignant melanomas, gliomas, neuroblastomas, pheochromocytomas, colon, renal, prostate and breast carcinomas and the like are aggressive forms of cancer, the early detection and treatment of which are of paramount importance. If left undetected or untreated, for several years or even months, the median survival time of patients having these types of cancers is dramatically reduced.

Of these cancers, lung cancer has led to the highest number of fatalities. In 1992 alone, lung cancer caused about 165,000 deaths within the United States. Two major types of lung carcinomas are responsible for most of these deaths: small cell lung carcinomas (SCLC) and nonsmall cell lung carcinoma (NSCLC).

SCLC is a neuroendocrine tumor that secretes several peptide growth factors including bombesin/gastrin releasing peptide (BN/GRP). SCLC is responsive to chemotherapy and radiation therapy, but relapse occurs frequently, and the median survival time is only about one year.

NSCLC accounts for about 75% of all lung cancer cases and encompasses a variety of carcinomas including adenocarcinomas, large cell carcinomas and squamous cell carcinomas. NSCLC tumors secrete transforming growth factor-alpha (TGF-$\alpha$) to stimulate cancer cell proliferation. NSCLC is generally treated with chemotherapy and surgical resection. However, the median survival time for patients with NSCLC is only about 5 years.

Melanomas are among the most serious manifestations of skin cancer and lead to a greater number of fatalities than any other form of skin cancer. Melanomas can metastasize through the lymphatic system to regional nodes and then via the blood to secondary sites on the skin or in the liver, lungs and brain. Whereas the prognosis for superficial spreading melanomas can be quite good, there is a much poorer prognosis for nodular melanomas in which distant metastases frequently form.

Breast cancer is a major cause of death for women, and estrogen receptors have been reported to play a major role in the development and growth of breast tumors. Deprivation of estrogen is one of the clinically effective methods for the treatment of breast cancer patients. Several growth factors such as insulin-like growth factor I (IGF-1), transforming growth factors (TGF-$\alpha$ and -$\beta$), epidermal growth factor (EGF), and platelet-derived growth factors have been shown to be involved in the growth and progression of human breast cancer cells. Some growth factors such as TGF-$\beta$ act as inhibitors of tumor growth. Despite the development of numerous antiestrogen compounds and other drugs, the clinical utility of antiestrogen is limited due to resistance by the tumor cells.

Many lives could be saved if lung carcinomas, melanomas, gliomas, neuroblastomas, pheochromocytomas, colon, prostate and renal carcinomas, breast tumors and the like were detected and treated at an early stage. Moreover, many patients are reluctant to undergo radical surgical or broad spectrum chemotherapy procedures which are frequently used to treat such cancers because these procedures can cause disfiguration and/or disablement.

Current techniques diagnose breast cancer by first identifying suspect tumors by single plane or 2D mammography screening. A biopsy is then required to differentiate tumors from other lesions. In the United States alone, 21 million mammographies are performed each year; 700,000 suspect tumors are biopsied and 182,000 women are diagnosed with breast cancer. This suggests that 400,000–500,000 women are subject to unnecessary biopsy each year.

Accordingly, an outstanding need exists for highly selective and non-invasive procedures permitting early detection and treatment of cancer.

A variety of radiopharmaceuticals have been evaluated for diagnostic imaging. For example, Michelot, J. M. et al. (1991 *J. Nucl. Med.* 32:1573–1580; Meyniel G. et al. (1990 *C.R. Acad. Sci. Paris* 3II (I): I3–18; and French Patent Publication No. 2,642,972 by Morean et al. have disclosed [$^{123}$I] and [$^{125}$I]N-(diethylaminoethyl)4-iodobenzamide (i.e. IDAB) for imaging malignant melanoma in humans. Unfortunately, the synthesis of IDAB is problematic and, more significantly, IDAB is taken up in high concentrations by non-melanoma cells in the liver and lung. Accordingly, IDAB does not have optimal specificity for melanoma cells and its uptake by non-tumor cells undermines its utility for routine screening of cancer.

The present invention provides compounds and complexes which bind with high specificity and affinity to receptors on a cancer cell surface. One such receptor is a sigma receptor. Sigma receptors are known to be present on neural tissues and certain immortalized neuroblastoma and glioma cell lines (Walker et al., 1990 Pharmacol. Reviews 42: 355–400; and Villner et al., *Multiple Sigma and PCP Receptor Ligands: Mechanisms for Neuromodulation and Neuroprotection* 341–53 (Kamenka et al., eds. NPP Books) (1992). However, it has been surprisingly found by the present inventors that sigma receptors are prevalent on some types of cancer cells, e.g., neuroblastoma, melanoma, glioma, pheochromocytoma colon, renal, prostrate and lung carcinoma cells. Recently, John et al. have found that MCF-7 breast tumor cells express sigma receptors. John et al., J. Med. Chem. 37:1737–1739 (1994).

Sigma receptors exist in at least two distinct subtypes termed sigma-1 and sigma-2. S. B. Hellewell, et al., A sigma-like binding site in rat pheochromocytoma (PC12) cells: Decreased affinity for (+)-benzomorphans and lower molecular weight suggest a different sigma receptor form from that in guinea pig brain, Brain Res. 527:244–253 (1990); R. Quirion, et al., A proposal for the classification of sigma binding sites, Trends in Pharmacol. Science 13:85–86 (1992). Tritiated sigma ligand probes such as (+)-pentazocine (a sigma-1 selective ligand), W. D. Bowen, et al., [$^3$H](+)-Pentazocine: A potent and highly selective benzomorphan-based probe for sigma-1 receptors, Mol. Neuropharmacol. 3:117–126 (1993); B. R. de Costa, et al., Synthesis and evaluation of optically pure [$^3$H](+)-pentazocine, a highly potent and selective radioligand for sigma receptors, FEBS Letters 251:53–58 (1989); and tritiated I,3-o-ditolylguanidine (DTG, a sigma non-subtype selective ligand), E. Weber, 1,3-Di(2-[5-$^3$H]tolyl)guanidine: a selective ligand that labels sigma type receptors for psychotomimetic opiates and antipsychotic drugs, Proc.

Natl. Acad. Sci. USA 83:8784–8788 (1986), have been used to characterize the expression of sigma receptors on various human tumor cell lines and to establish the pharmacological profiles for various drugs.

A very high density of both sigma-1 and sigma-2 receptor subtypes have been expressed on many human and rodent tumor cell lines (Bmax=1000–4000 fmol/mg protein). B. J. Vilner, et al., Sigma-1 and Sigma-2 receptors are expressed in a wide variety of human and rodent tumor cell lines, Cancer Res. 55:408–413 (1995). High levels of sigma receptors have also been reported in membrane preparations obtained from surgically removed solid human tumor tissue using [$^3$H]DTG. G. E. Thomas, Sigma and opioid receptors in human brain tumors, Life Sci. 46:1279–1286 (1990); W. T. Bem, et al., Overexpression of sigma receptors in non-neural human tumors; Cancer Res. 51:6558–6562 (1991).

Scatchard's analysis of 4-[$^{125}$I]-4-(N-benzylpiperidin-4-yl)-4-iodobenzamide binding in human breast adenocarcinoma (MCF-7) cells revealed that breast cancer cells possess approximately a million receptors per cell. C. S. John, et al., Synthesis and pharmacological characterization of 4-[125I]-N-(N-benzylpiperidin-4-yl)-4-iodobenzamide: a high affinity sigma receptor ligand for potential imaging of breast cancer, Cancer Res. 55:3022–3027 (1995).

A high density of sigma receptors has also been found on membranes prepared from human breast biopsy tissues. This can be compared to normal breast tissue, which has essentially no sigma receptors. C. S. John, et al., Characterization of sigma receptor binding sites in human biopsied solid breast tumors, J. Nucl. Med. 37:267P (1996)(abstract).

Furthermore, sigma receptors expressed in human melanoma cells, breast cancer cells, non-small cell lung carcinoma, and human prostate tumor cells have been characterized using different radio-iodinated sigma ligands. C. S. John, et al., A malignant melanoma imaging agent: synthesis, characterization, in vitro binding and biodistribution of iodine-125-(2-piperidinyiaminoethyl)4-iodobenzamide, J. Nuc. Med. 34:2169–2175 (1993); C. S. John, et al., Synthesis and characterization of [$^{125}$I]-N-(N-benzylpiperidin-4-yl)-4-iodobenzamide, a new sigma receptor radiopharmaceutical: high affinity binding to MCF-7 breast tumor cells, J. Med. Chem. 37:1737–1739 (1994); C. S. John, et al., Sigma receptors are expressed in human non-small cell lung carcinoma, Life Sci. 56:2385–2392 (1995); C. S. John, et al., Characterization and targeting of sigma receptor binding sites in human prostate tumor cells, J. Nucl. Med. 37:205P (1996)(abstract); C. S. John, et al., Synthesis, in-vitro binding and pharmacokinetics of radio-iodinated (N-benzylpiperidin-4-yl)-2-iodobenzamide: sigma receptor marker for human prostate tumors, (manuscript submitted).

From this information, the inventors concluded that sigma receptors were potential targets for the development of diagnostic probes. Consequently, the inventors embarked on a study of Tc-99m radiolabeled chelates that would bind to the sigma sites. Tc-99m is a widely used radionuclide in clinical nuclear medicine due to its instant availability from the Mo-99/Tc-99m generator, ideal physical properties (t$_{1/2}$=6.02 hrs; gamma energy=140 keV), absence of beta emissions, low radiation burden to patients and low cost.

However, it can be difficult to develop receptor based Tc-99m radiopharmaceuticals for diagnostic imaging. In order to provide in vivo stability to the radiolabel, Tc-99m has to be complexed to a chelate. Thus, it is necessary to synthesize a molecule suitable for imaging a particular receptor site such that it possesses a chelating moiety and a pharmacological moiety (i.e., a pharmacophore appended to the chelate moiety. For example, compounds specific for progestin receptors have been described. J. P. DiZio, et a., Technetium- and rhenium-labeled progestins: synthesis, receptor binding and in-vivo distribution of an 11-substituted progestin labeled with technetium-99 and rhenium-186, J. Nucl. Med. 33:558–569 (1992); J. P. O'Neil, et al., Progestin radiopharmaceuticals labeled with technetium and rhenium: synthesis, binding affinity, and in-vivo distribution of a new progestin N$_2$S$_2$-metal conjugate, Bioconjugate Chem. 5:182–193 (1994)

Furthermore, addition of a chelating moiety to a pharmacological entity often results in an increase in steric bulk of the molecule. Frequently, therefore, the molecule's affinity for the receptors can be compromised. John A. Katzenellenbogen, Designing Steroid Receptor-Based Radiotracers to Image Breast and Prostate Tumors, J. Nuclear Med. 36:8S–13S (1995).

There are other problems that arise when moving beyond imaging of tumors to treatment of tumors. Treatment of tumors, particularly the above mentioned tumors, can involve very large dosages of therapeutic materials. For example, chemotherapeutic materials may be administered in amounts on the order of 10–100 milligrams for a 70 kg normal adult. Such high dosages are needed because of the lack of specificity of the chemotherapeutic compounds for the tumors. The high dosages also lead to side effects, such as nausea, hair loss and vomiting, that can severely weaken a patient with a tumor or tumors. Therefore, it would be desirable to develop materials that could be administered in a much smaller amount, such that the severity of the side effects would be lessened.

SUMMARY OF THE INVENTION

Accordingly, the present invention is directed to compounds, complexes, compositions, and methods that substantially obviate one or more of the above discussed problems due to limitations and disadvantages of the related art.

In one aspect, the invention is directed to compound, for use in radioimaging and radio therapy, of the formula K$_1$ or K$_2$

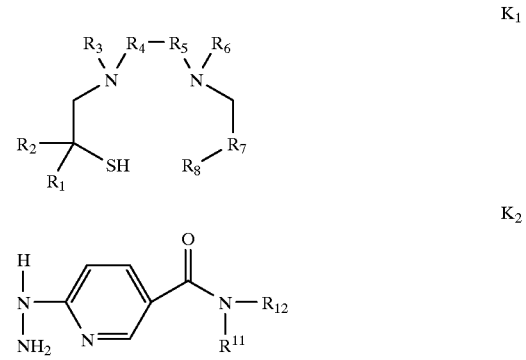

wherein R$_1$, R$_2$, and R$_4$ are H or Me; R$_3$ is H, lower alkyl, lower alkylene, cycloalkyenyl, aryl, or arylalkane;

$R_4$ and $R_5$ are

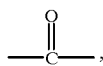,

—$CH_2$—, or

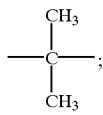;

$R^6$ is —$(CH_2)_j$—CZ—$NR_{10}$—$(CH_2)_m$—$R_9$,

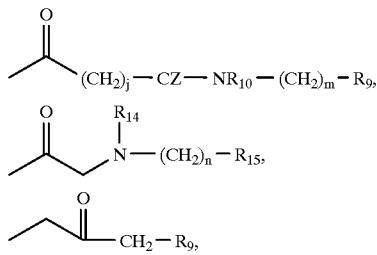

or hydrogen;
$R_7$ is

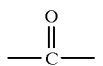

or —$CH_2$—;
$R_8$ is —SH, or

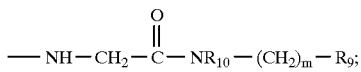

$R_9$ and $R_{15}$ are —$N(R_{10})_2$ or a 5 to 7 membered heterocyclic ring, containing nitrogen, oxygen, or sulfur, the ring being unsubstituted or substituted with at least one alkyl or arylalkyl substitutent, said heterocyclic ring containing 2–6 ring carbon atoms and 1–3 ring heteroatoms; $R_{10}$ and $R_{14}$ are independently lower alkyl or hydrogen;
$R_{11}$ is hydrogen or methyl;
$R_{12}$ is —CZ—$NR_{10}$—$(CH_2)_m$—$R_9$ or

wherein $R_{13}$ is hydrogen or methyl; Z is oxygen or 2 hydrogen atoms; m is an integer from 0 to 6; n is an integer from 1 to 6; and j is an integer from 0 to 6; wherein if m is zero then $R_9$ is hydrogen or lower alkyl.

In a preferred embodiment, the invention is directed to complexes comprising compounds of the formula $K_1$ and $K_2$ and $^{99m}Tc((V)0$, $Re(v)0$, $In^{+3}$, $^{67}Ga^{+3}$, $^{90}Y^{+3}$, $^{109}Pd^{+2}$ or $^{105}Rh^{+3}$. Another preferred embodiment is directed to compositions comprising a diagnostic imaging amount of at least one complex comprising compounds of the formula $K_1$ and $K_2$ and $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$ together with a pharmaceutically acceptable carrier therefor. In yet another preferred embodiment, the invention is directed to such compositions wherein the complex contains $^{99m}Tc(V)0$ Another preferred aspect of the invention is a method for diagnosing a tumor in a mammal comprising the steps of administering to the mammal a diagnostic imaging amount of a complex as described above, and detecting an image of a tissue having an abundance of cells with sigma receptors. A further preferred aspect of the invention is a method for in vitro detection of a cancer cell in a mammalian tissue sample comprising the step of contacting the mammalian tissue sample with a complex as described above, and detecting cells with an abundance of sigma receptors.

Yet another preferred embodiment of the invention is a method for treating a tumor in a mammal comprising the step of administering to the mammal a radiotherapeutic amount of a complex as described above, wherein the complex includes $Re(V)0$, $In^{+3}$, $^{67}Ga^{+3}$, $^{90}Y^{+3}$, $^{109}Pd^{+2}$ or $^{105}Rh^{+3}$. In another preferred embodiment, the invention is directed to the method for treating tumors in mammals wherein the tumor is: lung carcinoma, melanoma, glioma, neuroblastoma, pheochromocytoma, colon, prostate and renal carcinoma or breast tumor.

In a preferred embodiment, the method for treating tumors in mammals comprises the step of administering to the mammal at least one complex as described above, wherein the complex includes $Re(V)0$, $In^{+3}$, $^{67}Ga^{+3}$, $^{90}Y^{+3}$, $^{109}Pd^{+2}$ or $^{105}Rh^{+3}$, and wherein the complex is administered in both a diagnostic imaging and a radio therapeutic amount.

BRIEF DESCRIPTIONS OF THE DRAWINGS

DETAILED DESCRIPTION OF THE INVENTION

Figure 1:
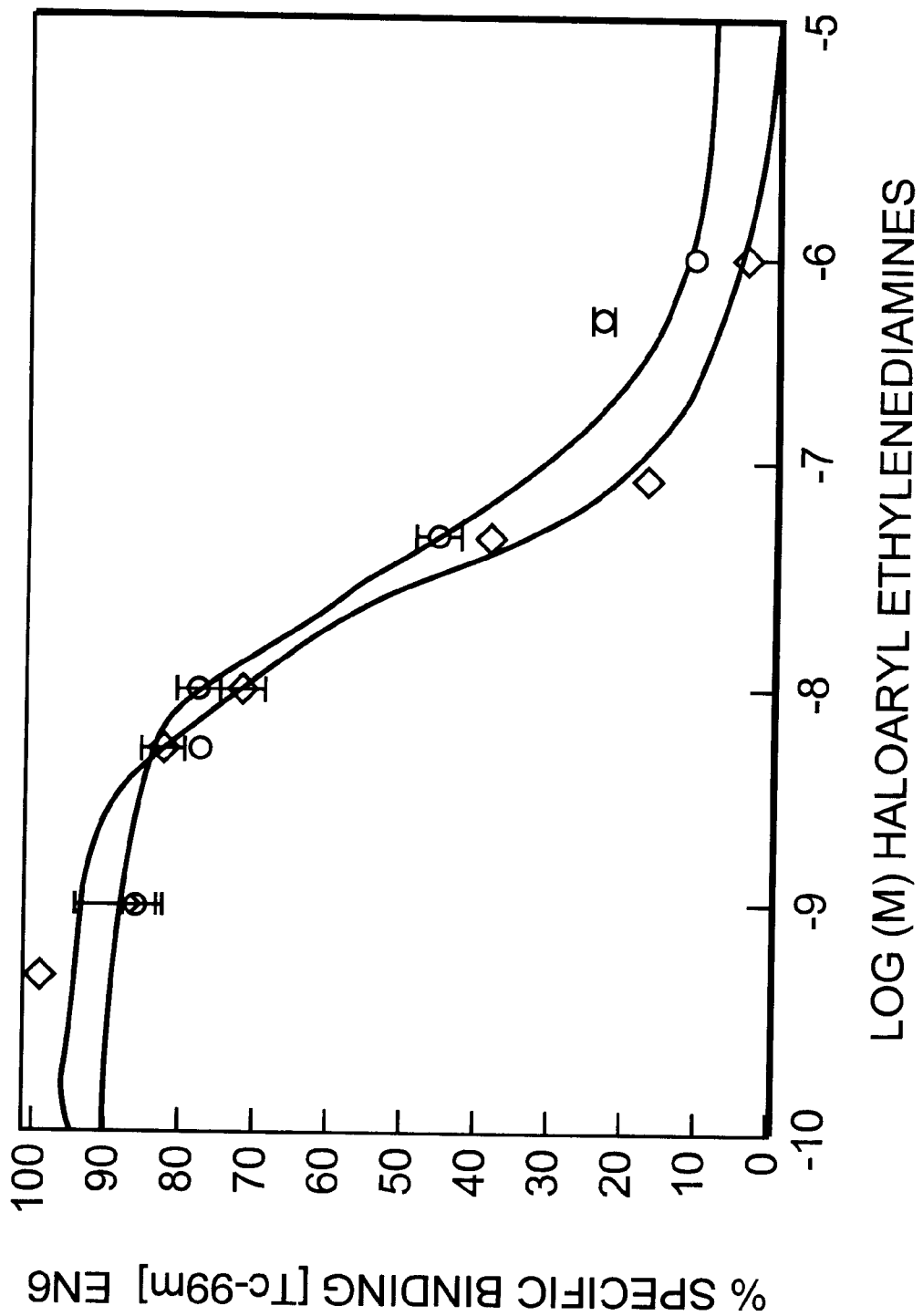
FIG. 1 shows inhibition of [Tc-99m]EN6 binding with substituted haloaryl ethylenediamines.

The present invention provides novel compounds, complexes, compositions, kits, and methods for detecting and treating certain types of cancer, e.g. neuroblastomas, gliomas, pheochromocytomas, melanomas, colon, renal, prostate, lung and breast carcinomas.

In recent years, some progress has been made for imaging steroid receptors, muscarinic receptors, and vesamicol receptors using bisaminothiol based Tc-99m chelates. S. Z. Lever, et al., Novel technetium ligands with affinity for the muscarinic cholinergic receptors, Nucl. Med. Biol. 21:157–164 (1994); R. B. Del Rosario, et al., Synthesis and in vivo evaluation of a 99m/99Tc-DADT-benzovesamicol: a potential marker for cholinergic neurons, Nucl Med. Biol. 21:197–203 (1994), all of which are hereby incorporated by reference.

Halogen-substituted arylethylenediamines have been studied extensively for their sigma affinities. B. R. de Costa, et al., Synthesis, characterization and biological evaluation of a novel class of N-(arylethyl)-N-alkyl-2-(1-pyrrolidinyl) ethylamines: structural requirements and binding affinity at the sigma receptors, J. Med. Chem. 35:38–47 (1992); B. R. de Costa, et al. Synthesis and receptor binding properties of fluoro- and iodo-substituted high affinity sigma receptor ligands: Identification of potential PET and SPECT sigma receptor imaging agents, J. Med. Chem. 35:2221–2230 (1992), all of which are hereby incorporated by reference.

BD 1008 {N-2(3,4-dichlorophenyl)ethyl]-N-methyl-(2-pyrrolidinyl) ethylamine), is one of the most potent halogenated arylethylenediamine derivatives. One congener of this series, [$^{125}$I]N-[2-(4-iodophenyl)ethyl]-N-methyl-2-(1-piperidinyl)ethylamine, 4-[$^{125}$I]PEMP, has recently been studied. C. S. John, et al., Synthesis binding characteristics and in-vivo clearance of 4-[I-125]PEMP: a sigma receptor ligand for imaging tumors, J. Nucl. Med. 36:6P (1995) (abstract); C. S. John, et al., Synthesis, in vitro validation and in vivo pharmacokinetics of [$^{125}$I]N-[2-(4-iodophenyl)ethyl]N-methyl-2-(1-piperidinyl)ethylamine: a high affinity ligand for imaging sigma receptor positive tumors, Nucl. Med. Biol. 23:761–766 (1996), all of which are hereby incorporated by reference.

This compound showed very high specific binding to the sigma receptors of human breast and melanoma tumor cells. The inhibition binding isotherms for 4-[$^{125}$I]PEMP in guinea pig brain also were consistent with sigma receptor pharmacology. The structure-activity relationship of de Costa et al., suggested that the substituted ethylenediamine portion of the molecule is the molecular recognition fragment that imparts high affinity for a sigma receptor, with the halogen substituted aromatic ring occupying the lipophilic pocket of the receptor. Therefore, pharmacophores, such as N-methyl-2-piperidinyl ethylamine, were appended to chelates, such as bisaminoethanethiol, to test the hypothesis that the molecular recognition fragment would impart specificity for the sigma receptors to the resulting Tc-99m labeled complex.

However, as noted above, addition of a chelating moiety to a pharmacological entity can result in an increase in steric bulk of the molecule compromising the affinity for the receptors. John A. Katzenellenbogen, Designing Steroid Receptor-Based Radiotracers to Image Breast and Prostate Tumors, J. Nuclear Med. 36:8S–13S (1995), which is hereby incorporated by reference. In addition, experimentation with several other structural parameters such as lipophilicity, charge, and the pharmacophore's biological activity were confirmed. Poor selections of any of these parameters could have resulted in an inactive molecule.

Surprisingly, the compounds and complexes of the present invention developed by the inventors can bind to sigma receptors, which are prevalent on lung carcinoma, colon carcinoma, renal carcinoma, melanoma, glioma, pheochromocytoma, neuroblastoma, prostate carcinomas, breast carcinomas and the like cancer cells. Compounds or complexes according to the invention, possessing the sigma pharmacophore, can be useful for diagnostic imaging of sigma receptor-positive tumors, and for radiotherapeutic treatment of such tumors.

Accordingly, in one aspect, the invention is directed to compound, for use in radioimaging and radio therapy, of the formula $K_1$ or $K_2$ $K_1$

[structure: $R_3$, $R_4$—$R_5$, $R_6$ on N—N with $R_2$, $R_1$, SH, $R_8$, $R_7$]

-continued $K_2$

[structure: H-N(NH$_2$)-pyridine-C(O)-N($R_{11}$)-$R_{12}$]

wherein:

$R_1$ and $R_2$ are H or Me;

$R_3$ is H, lower alkyl, lower alkylene, cycloalkyenyl, aryl, or arylalkane; $R_4$ and $R_5$ are $$-\overset{O}{\underset{\|}{C}}-,$$

—CH$_2$—, or $$-\overset{CH_3}{\underset{CH_3}{\overset{|}{\underset{|}{C}}}}-;$$

$R^6$ is —(CH$_2$)$_j$—CZ—NR$_{10}$—(CH$_2$)$_m$—R$_9$,

[structure: ketone-(CH$_2$)$_j$—CZ—NR$_{10}$—(CH$_2$)$_m$—R$_9$]

[structure: ketone with $R_{14}$, N—(CH$_2$)$_n$—R$_{15}$,]

[structure: ketone-CH$_2$—R$_9$,]

or hydrogen;

$R_7$ is $$-\overset{O}{\underset{\|}{C}}-$$

or —CH$_2$—;

$R_8$ is —SH, or $$-NH-CH_2-\overset{O}{\underset{\|}{C}}-NR_{10}-(CH_2)_m-R_9;$$

$R_9$ and $R_{15}$ are —N(R$_{10}$)$_2$ or a 5 to 7 membered heterocyclic ring, containing nitrogen, oxygen, or sulfur, the ring being unsubstituted or substituted with at least one alkyl or arylalkyl substitutent, said heterocyclic ring containing 2–6 ring carbon atoms and 1–3 ring heteroatoms; $R_{10}$ and $R_{14}$ are independently lower alkyl or hydrogen; $R_{11}$ is hydrogen or methyl;

$R_{10}$ is —CZ—$NR_{10}$—$(CH_2)_m$—$R_9$ or

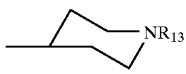

wherein $R_{13}$ is hydrogen or methyl; Z is oxygen or 2 hydrogen atoms; m is an integer from 0 to 6; n is an integer from 1 to 6; and j is an integer from 0 to 6, wherein if m is zero then $R_9$ is hydrogen or lower alkyl.

The invention is also directed to a compound wherein the compound is

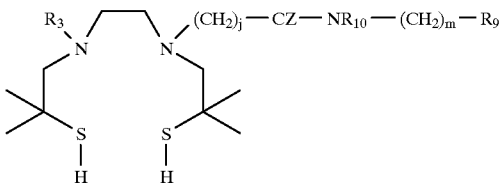

wherein Z, j, m, $R_3$, $R_9$, and $R_{10}$ are as defined above.

The invention is also directed to a compound, wherein the compound is

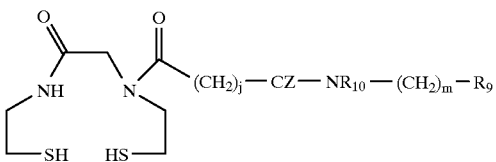

wherein Z, j, m, $R_9$ and $R_{10}$ are as defined above.

In another aspect, the invention is directed to a compound, wherein the compound is:

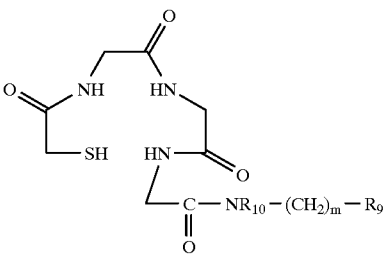

wherein j, m, $R_9$, and $R_{10}$ are as defined above.

In yet another aspect, the invention is directed to a compound wherein the compound is

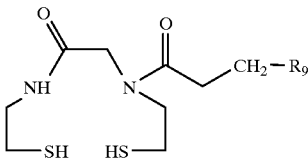

wherein $R_9$ is as defined above.

The invention is also directed to compounds of the formula $K_1$ and $K_2$ wherein $R_9$ is —$N(R_{10})_2$ and each $R_{10}$ is independently lower alkyl or hydrogen. In another aspect, the invention is directed to compounds of the formula $K_1$ and $K_2$ wherein $R_9$ is an N-linked 5 to 7 membered heterocyclic ring containing nitrogen which can have at least one alkyl substituent, said alkyl containing 1–6 carbon atoms, and said heterocyclic ring containing nitrogen including 2–6 ring carbon atoms and 1–3 ring heteroatoms of which at least one is nitrogen.

The invention is also directed to compounds of the formula $K_1$ and $K_2$ wherein said heterocyclic ring is

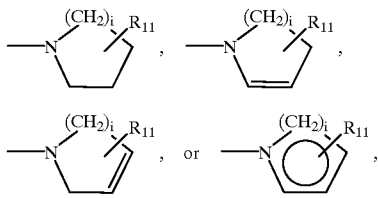

wherein i is an integer from 1 to 3 and $R_{11}$ is hydrogen or lower alkyl. The invention is further directed to such compounds wherein said heterocyclic ring is N-piperidinyl, N-pyrrolidinyl, N-pyridinyl, N-morpholinyl, N-pyrrolyl, or N-homopiperidinyl.

In another aspect the invention is directed to a compound of the formula $K_1$ and $K_2$ wherein said heterocyclic ring is:

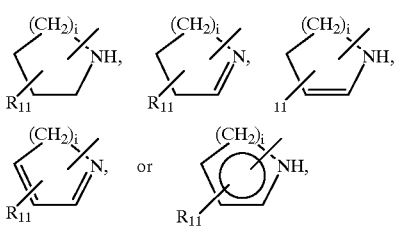

wherein i is an integer from 1 to 3 and $R_{11}$, is hydrogen or lower alkyl. Additionally, the invention is directed to compounds of the formula $K_1$ and $K_2$ wherein said heterocyclic ring is piperidenyl, pyrrolidinyl, pyridinyl, morpholinyl, homopiperidinyl or pyrrolyl.

In another embodiment, the invention is directed to compounds of the formula $K_1$ and $K_2$ wherein each $R_{10}$ is lower alkyl.

In another embodiment, the invention is directed to compounds of the formula $K_1$ and $K_2$ wherein each $R_{10}$ is hydrogen.

In another embodiment, the invention is directed to compounds of the formula $K_1$ and $K_2$ wherein j=2. In another embodiment, the invention is directed to compounds of the formula $K_1$ and $K_2$ wherein j=0.

In yet another embodiment, the invention is directed to compounds of the formula $K_1$ wherein $R_6$ is

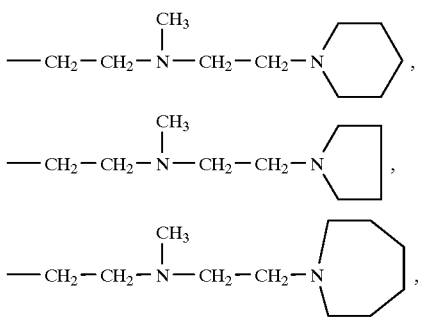

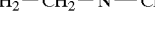

wherein $R_3$ and $R_4$ are as defined above.

In yet another aspect, the invention is directed to compounds of the following formulas:

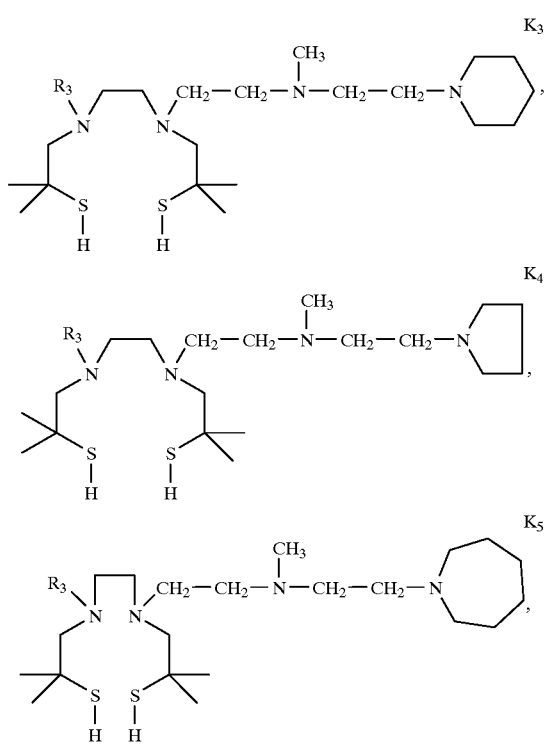

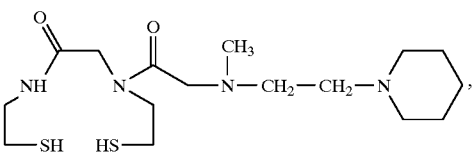

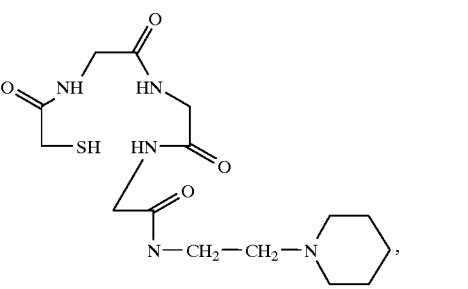

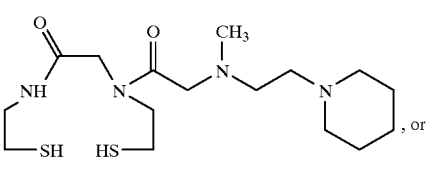

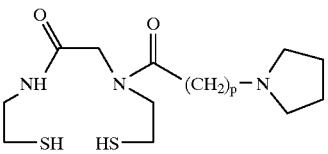

wherein $R_3$ and $R_{10}$ are as defined above and p=1 to 6.

In another aspect, the invention is direct to complexes comprising compounds of the above formulas and $^{99m}Tc(V)O$, $Re(V)O$, $In^{+3}$, $^{67}Ga^{+3}$, $^{90}Y^{+3}$, $^{109}Pd^{+2}$ or $^{105}Rh^{+3}$.

In a further aspect of the invention, compositions are disclosed that comprise a diagnostic imaging amount of at least one complex comprising compounds of the above formulas and $^{99m}Tc(V)O$, $Re(V)O$, $In^{+3}$, $^{67}Ga^{+3}$, $^{90}Y^{+3}$, $^{109}Pd^{+2}$ or $^{105}Rh^{+3}$, and a pharmaceutically acceptable carrier therefor. In a preferred embodiment, the compositions contain at least one complex that contains $^{99m}Tc(V)O$.

In a further aspect of the invention, compositions are disclosed that comprise a radiotherapeutic amount of at least one complex comprising compounds of the above formulas and $Re(V)O$, $In^{+3}$, $^{67}Ga^{+3}$, $^{90}Y^{+3}$, $^{109}Pd^{+2}$ or $^{105}Rh^{+3}$, and a pharmaceutically acceptable carrier therefor. Yet another aspect of the invention is a method for diagnosing a tumor in a mammal comprising the steps of administering to the mammal a diagnostic imaging amount of a complex as described above, and detecting an image of a tissue having an abundance of cells with sigma receptors.

A further embodiment of the invention is a method for in vitro detection of a cancer cell in a mammalian tissue sample comprising the step of contacting the mammalian tissue sample with a complex as described above, and detecting cells with an abundance of sigma receptors.

Yet another embodiment is a method for treating a tumor in a mammal comprising the step of administering to the mammal a radiotherapeutic amount of a complex or composition as described above, wherein the complex includes $Re(V)O$, $In^{+3}$, $^{67}Ga^{+3}$, $^{90}Y^{+3}$, $^{109}Pd^{+2}$ or $^{105}Rh^{+3}$. In another embodiment of this method, the tumor is: lung carcinoma, melanoma, glioma, neuroblastoma, pheochromocytoma, colon, prostate and renal carcinoma or breast tumor. Another embodiment of the invention is a method for detecting a tumor in a mammal comprising the step of administering to the mammal at least one complex as described above, wherein the complex includes Re(V)0, In$^{+3}$, $^{67}$Ga$^{+3}$, $^{90}$Y$^{+3}$, $^{109}$Pd$^{+2}$ or $^{105}$Rh$^{+3}$, and wherein the complex is administered in an amount that is both a diagnostic imaging and a radio therapeutic amount.

According to the present invention Z is oxygen or two hydrogen atom substituents. Because the —CZ-moiety is adjacent to an amine, when Z is oxygen, an amide (—CO—NH—) is formed. When Z is two hydrogen atoms, a methylene (—CH$_2$—) is formed. Therefore, embodiments of the present invention can have amide or alkylamino moieties, e.g. one of the following side chains:

—(CH$_2$)$_j$—CO—NR$_{10}$—(CH$_2$)$_m$—R$_9$ or

—(CH$_2$)$_j$—CH$_2$—NR$_{10}$—(CH$_2$)$_m$—R$_9$.

The variable j, as used herein, refers to an integer ranging from 0 to 6 which defines the length of the alkylene chain separating the chelant and —CZ-moieties of the present invention. Preferably, j is an integer from 0 to 3. More preferably, j is an integer from 0 to 2.

The variable m defines the length of the alkylene chain separating the —CZ—NR$_{10}$— and the R$_9$ group in the —CZ—NR$_{10}$—(CH$_2$)$_m$—R$_9$ moiety. The variable m is an integer ranging from 0 to 6. However, m is preferably 0 to 4 and more preferably 0 to 3.

The variable n is an integer from 1 to 6. The variable p is an integer from 1 to 6.

In a preferred embodiment Z is oxygen, i.e., the —CZ— group forms a carbonyl. Alternatively, when —CZ—NR$_{10}$— is —CH$_2$—NR$_{10}$—, the R$_{10}$ is preferably lower alkyl. Furthermore, when m equals zero, R$_9$ and R$_{10}$ may be, independently of each other, hydrogen, lower alkyl, or may form a heterocyclic ring with the nitrogen atom adjacent to R$_{10}$.

As provided herein R$_3$ is independently H, lower alkyl, lower alkylene, cycloalkenyl, aryl, or arylalkane. In a preferred embodiment R$_3$ is H or lower alkyl.

Further, R$_{10}$ and R$_{14}$ are independently hydrogen or lower alkyl.

As provided herein, R$_9$ and R$_{15}$ may be an N-linked 5 to 7 membered heterocyclic ring containing nitrogen which can have at least one alkyl substituent. As defined herein N-linked means that the heterocyclic ring containing nitrogen is attached to the main chain through a nitrogen atom. Preferred R$_9$ heterocyclic ring include rings of the formulae:

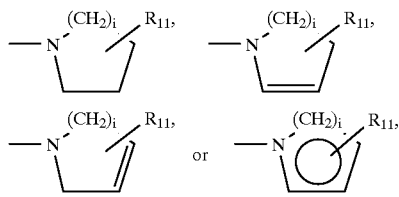

wherein R$_{11}$ is hydrogen or lower alkyl and each i is an integer from 1 to 3.

In preferred embodiment, R$_9$ may be a heterocyclic ring not attached via the ring wherein each i is independently an integer from 1 to 3 and R$_4$ is hydrogen or lower alkyl or arylalkyl.

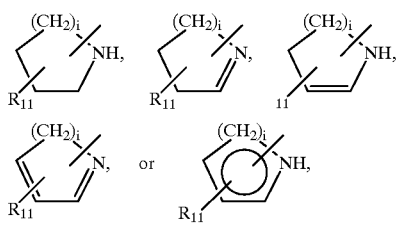

Preferred R$_9$ heterocyclic rings include N-piperidinyl, N-pyrrolidinyl, N-pyridinyl, N-morpholinyl, N-pyrrolyl, N-homopiperidinyl, piperidinyl, pyrrolidinyl, pyridinyl, morpholinyl or pyrrolyl, which can be substituted with a lower alkyl or arylalkyl, which is preferably attached to the nitrogen of the piperidinyl, pyrrolidinyl or morpholinyl rings.

R$_9$ may also be an —N(R$_{10}$)$_2$ group in which R$_{10}$ is hydrogen or lower alkyl. In a preferred embodiment for —N(R$_{10}$)$_2$, R$_{10}$ is lower alkyl.

The term lower alkyl, when used singly or in combination, refers to alkyl groups containing one to six carbon atoms. Lower alkyls may be straight chain or branched and include such groups as methyl, ethyl, propyl, isopropyl, butyl, sec-butyl, isobutyl, t-butyl, pentyl isopentyl, neopentyl, hexyl and the like. The preferred alkyl groups contain one to four carbon atoms.

As used herein, a lower alkylene, singly or in combination with other groups, contains up to six carbon atoms in the main chain and a total of 10 carbon atoms if the alkylene is branched. Lower alkylene groups include methylene, ethylene, propylene, isopropylene, butylene, t-butylene, sec-butylene, isobutylene, amylene, isoamylene, pentylene, isopentylene, hexylene and the like. The preferred lower alkylene groups contain one to four carbon atoms.

The term cycloalkenyl refers to a partially saturated cyclic structure, i.e., a ring, having 3–7 ring carbon atoms which can have one or two unsaturations. Because the cycloalkenyl groups of the present invention are fused to a phenyl moiety, such cycloalkenyls are partially unsaturated. The subject cycloalkenyl groups include such groups as cyclopropenyl, cyclobutenyl, cyclopentenyl, cyclohexenyl and cycloheptenyl rings.

Aryl refers to moieties having ring structures characteristic of benzene, naphthalene, phenanthrene, etc. These moieties have either the six-carbon ring of benzene or the condensed six-carbon rings of other aromatic derivatives. A preferred aryl group is phenyl, C$_6$H$_5$.

The term arylalkane refers to moities containing both aliphatic and aryl structures. A preferred arylalkane is benzyl, CH$_2$C$_6$H$_5$.

As employed herein, a heterocyclic ring means a saturated, partially saturated or aromatic heterocyclic ring having at least one nitrogen, oxygen, or sulfur ring atom. As is known to the skilled artisan a saturated heterocyclic ring has no double bonds. As used herein a partially saturated heterocyclic ring can have at least one double bond.

The present heterocyclic rings can have 1–3 ring heteroatoms and 2 to 6 ring carbon atoms. Preferably, a heterocyclic ring has at least one nitrogen heteroatom. Heterocyclic rings can also have a mixture of nitrogen and oxygen heteroatoms, e.g. morpholine with one oxygen and one nitrogen. It is preferred that the heterocyclic ring contain one or two ring heteroatoms; a more preferred embodiment being one ring nitrogen or oxygen heteroatom.

Heterocyclic rings of the present invention may be monocyclic; such monocyclic rings can be fused to a phenyl ring to form a bicyclic ring.

Representative partially saturated and heteroaromatic heterocyclic rings include furan, pyran, oxazine, isoxazine, pyrrole, pyrazole, pyridine, pyridazine, furan, homopiperidine, piperidine, pyrrolidone, morpholine, and the like. Preferred heteroaromatic groups include pyridine and the like. Representative saturated heterocyclic rings include tetrahydrofuran, pyrazolidine, imadazolidine, pyrrolidine, azetidine, piperidine, piperazine and morpholine.

The various combinations and permutations of the Z, $R_1$, $R_2$, $R_3$, $R_4$, $R_5$, $R_6$, $R_7$, $R_8$, $R_9$, $R_{10}$, $R_{11}$, $R_{12}$ and $R_{13}$ described herein are contemplated to be within the scope of the present invention. Moreover, the present invention also encompasses compounds and complexes which contain less than all of the substituents in the Markush grouping. Thus, the present compounds and complexes contain one or more substitutents of each of the Markush groupings in Z, $R_1$, $R_2$, $R_3$, $R_4$, $R_5$, $R_6$, $R_7$, $R_8$, $R_9$, $R_{10}$, $R_{11}$, $R_{12}$ and $R_{13}$ and the various combinations thereof. For example, the present invention contemplates that $R_9$ may be one or more of the substituents listed hereinabove or any and all of the substituents of $N(R_{10})_2$.

The binding characteristics of the present compounds can be determined by observing whether binding was inhibited by known sigma receptor ligands using techniques known to one of skill in the art. Many ligands are known which have demonstrated binding specificities for a given cell surface receptor. Such ligands can be tested as competitive inhibitors for cellular binding by compounds or complexes of the present invention. If a given ligand is a competitive inhibitor, the receptor to which the ligand binds must also bind the subject compounds or complexes.

For example, a malignant melanoma cell line may bind the present compounds or complexes with high specificity and affinity. Only ligands which bind to the same site as the present compounds or complexes can inhibit binding of the subject compounds. Ligands which can be tested include ligands specific for cell receptors such as sigma (e.g., haloperidol, arylethylenediamines, DTG, benzomorphans, and iodobenzamides), sigma-1 (e.g. (+)-pentazocine), sigma-2 (e.g. DTG in the presence of dextrallorphan), and the like.

As provided herein, ligands with demonstrated binding specificity for cell surface sigma receptors (e.g. haloperidol, arylethylenediamines, DTG, benzomorphans, and iodobenzamides) can act as competitive binding inhibitors for compounds or complexes of the present invention. In contrast, ligands that do not bind to cell surface sigma receptors cannot inhibit binding of the present compounds or complexes to cancer cells expressing sigma receptors.

Cell types which have sigma receptors include normal tissues such as brain, kidney, liver, etc., together with cancerous tissues such as lung carcinoma, colon carcinoma, renal carcinoma, breast and prostate carcinoma, melanoma, pheochromocytoma, glioma, neuroblastoma and the like.

Breast cancer cells, particularly MCF-7 tumor cells, have also demonstrated binding affinity for the present invention. In a preferred embodiment, the present invention can be used to detect and treat breast cancer. In another preferred embodiment, the present invention can be used to detect and treat breast cancer in women with dense breasts.

The present invention may be prepared as a complex and/or a composition for convenient and effective administration to a mammal for diagnostic imaging or radiotherapy. The compositions contain a diagnostic imaging amount or a radiotherapeutic amount of at least one of the present complexes together with a pharmaceutically acceptable carrier, in an appropriate dosage.

As used herein, a pharmaceutically acceptable carrier includes solvents, dispersion media, antibacterial and antifungal agents, isotonic agents, and the like which are physiologically acceptable. The use of such media and agents are well-known in the art.

The compounds or complexes according to the invention may be administered by conventional means, preferably by injection. The suitable forms for injection include sterile aqueous solutions or dispersions and sterile powders of the above mentioned chelate pharmacophores (1 mg to 3 mg), freeze dried along with stannous chloride (up to 1 mg) and the inactive fillers such as dextrose, glucose, etc (up to 20 mg). To this, sodium pertechnetate (up to 500 mCi) could be added to form chelate pharmacophore complexes that can be administered to patients.

The diagnostic imaging amounts are preferably about 1 to about 50 milliCuries (mCi) for a 70 kg normal adult, more preferably being about 1 to about 25 mCi for a 70 kg normal adult. Complexes containing $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$ may be used for diagnostic imaging.

A radiotherapeutic amount is an amount of at least one of the subject complexes that permit sufficient tumor localization of the complex to diminish tumor growth or size. As provided herein tumor growth or size can be monitored by any known diagnostic imaging procedure, e.g., by using the present methods.

Radiotherapeutic amounts as used herein are preferably about 1 to about 200 mCi for a 70 kg normal adult, more preferably about 1 to about 100 mCi for a 70 kg normal adult. This corresponds to a less than one milligram quantity of the inventive complex. This can be compared to the 10–100 milligram quantities of conventional chemotherapeutic materials. The significantly smaller administered quantity of the inventive complexes is reasonably expected to lead to significantly reduced undesirable pharmacological effects (i.e. side effects) in the patient. Preferred radiotherapeutic complexes include $Re(V)0$, $In^{+3}$, $^{67}Ga^{+3}$, $^{90}Y^{+3}$, $^{109}Pd^{+2}$ or $^{105}Rh^{+3}$. Of course, when considering a dosage for diagnostic imaging or therapy, the specific activity of the radioactive complex should be taken into consideration.

The ultimate solution form must be sterile. Sterilization can be accomplished by any art recognized technique, including but not limited to, addition of antibacterial of antifungal agents, for example, paraben, chlorobutanol, phenol, sorbic acid, thimerosal, and the like.

According to the present invention, methods for diagnosing a mammal for the presence of a mammalian tumor include administering to a mammal a complex or composition including a diagnostic imaging amount of at least one of the present complexes or compositions and detecting an image of a tissue having an abundance of cells with sigma receptors.

As described herein, an image of a tumor or tissue labeled with one or more of the present compounds can be detected using a radiation detector, e.g. a γ-radiation detector. One such procedure utilizes scintigraphy. Tomographic imaging procedures such as single photon emission computed tomography (SPECT) can also be used to improve visualization. Selection and use of such radiation detectors is within the skill of one of ordinary skill in the art.

In another embodiment, the present invention is directed to a method for treating a mammal having a mammalian tumor which includes administering to the mammal either a radiotherapeutic amount of at least one of the present complexes, or a composition including a radiotherapeutic amount of at least one complex of the present invention.

By proper selection of a complex or complexes according to the invention, it may be possible to detect and treat tumors in a single treatment or administration. Such a complex or complexes would be administered in both a diagnostic imaging and a radio therapeutic amount.

In yet another embodiment, the present invention provides a method for in vitro detection of a cancer cell in a mammalian tissue sample which includes contacting a mammalian tissue sample with an in vitro diagnostic imaging amount of a complex or composition according to the invention for a time and under conditions sufficient to permit binding to a cell surface sigma receptor on the cancer cell and detecting such binding.

Samples can be collected by procedures known to the skilled artisan, e.g., by collecting a tissue biopsy or a body fluid, by aspirating for tracheal or pulmonary samples and the like.

As used herein any mammalian tissue can be tested in vitro. Preferred tissues for in vitro testing include lung, bronchial, lymph, skin, brain, liver, prostate, breast, any tissue of nervous origin and the like. Samples can be sectioned, e.g., with a microtome, to facilitate microscopic examination and observation of bound compound. Samples can also be fixed with an appropriate fixative either before or after incubation with one of the present compounds to improve the histological quality of sample tissues.

Conditions sufficient for binding of the compound to a cell surface sigma receptor on the cancer cell include standard tissue culture conditions, i.e. samples can be cultured in vitro and incubated with one of the present compounds in physiological media. Such conditions are well known to the skilled artisan. Alternatively, samples can be fixed and then incubated with a compound of the present invention in an isotonic or physiological buffer.

An amount of at least one of the present complexes for in vitro detection of a cancer cell can range from about 1 ng/l to about 1000 μg/l. A preferred amount is about 1 μg/l to about 100 μg/l. When the present compounds are used for in vitro diagnosis of cancer, metal complexes containing $^{99m}Tc$ (V)0, Re(V)0, $In^{+3}$, $^{67}Ga^{+3}$, $^{90}Y^{+3}$, $^{109}Pd^{+2}$ or $^{105}Rh^{+3}$ may be used.

For detection of cellular binding of one of the present compounds, samples can be incubated in the presence of a selected compound, then washed and counted in a standard scintillation counter. Alternatively, samples can be dipped in photoemulsion and the signal detected under light microscopy after several days, as exposed silver grains.

The inventive compounds can be prepared from readily available starting materials, using conventional synthetic organic chemistry techniques.

The following Examples further illustrate the invention. As is recognized by the skilled artisan, the Examples for making the present compounds and complexes can be modified to include other known and commonly available procedures. The Examples provided herein are intended to be illustrative and are not exhaustive; therefore the illustrated Examples should not be viewed as limiting the invention in any way.

EXAMPLE 1

Synthesis of Dialkylated Bisaminothiol (BAT) Ligands

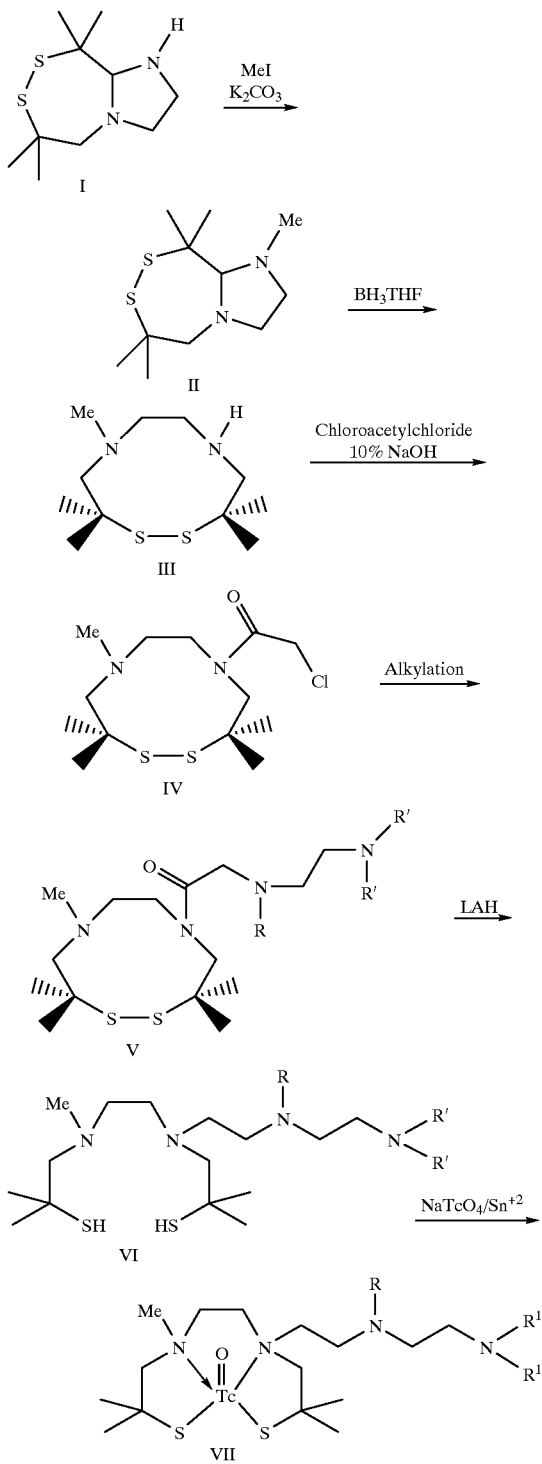

R' = Me, EI,
R = Me, EI

An exemplary procedure for synthesis of compounds of the formula $K_1$ begins with the general method for the preparation of this class of ligands. The starting material for the synthesis of dialkylated bisaminothiol is imidazolidino [1,2-d]dithiazepine, (I). This precursor may be prepared by the literature method of A. V. Joshua et al., J. Org. Chem. 52:2447–2451 (1987) incorporated herein. The synthesis is generally performed as follows. According to the synthesis, dithiazepine (I) is first alkylated with alkylhalide to give (II), and the bicyclic ring is then reduced to produce saturated ten-membered ring heterocycle (III). The secondary amine is acylated using chloroacetyl chloride and 10% NaOH to produce acylated derivative (IV). The alkylation of (IV) with an unsymmetrical amine is achieved using a slight excess of amine and 10% aqueous NaOH in methylene chloride to give tertiary amide (V). This amide is finally reduced to give dialkylated bisaminothiol ligand (VI) which is stored as a hydrochloride salt for complexation with Tc-99m (VII).

The synthesis is now described in more detail.

The first step is alkylation of imidazolidino[1.2-d] dithiazepine (I). To a stirred solution of I (5.0 g, 21.5 mmol) in ethanol (100 ml) is added anhydrous potassium carbonate (2.97 g, 21.5 mmol) and iodomethane (3.35 g, 23.6 mmol). The mixture is stirred at room temperature for 3 h. The reaction mixture is filtered and the organic layer is evaporated to give desired methylated derivative of dithiazepin (II).

Next, a solution of N-methylated dithiazepine (3.0 g, 12.3 mmol) in THF (100 mL) is heated at reflux for 12 h with borane-tetrahydrofuran solution (4 eq). The reaction mixture is quenched by adding dropwise an ethanolic HCl solution. The mixture is heated further for 3 h, the volatiles are removed in vacuo, and the residue is triturated with anhydrous ether to give the saturated heterocycle 5,8-diazacyclodecane (III).

Next, a solution of (III) (2.0 g, 8.1 mmol) in $CH_2Cl_2$ is added 10% aqueous solution of sodium hydroxide and 1.5 eq amount of the chloroacetylchloride. The mixture is stirred at room temperature for 3–5 h. The organic layer is separated, washed with water, dried, and the volatiles are removed in vacuo. The acyl derivatives (IV) subsequently obtained may be purified by column chromatography, if necessary.

Compound (IV) is then condensed with substituted ethylenediamines. A solution of substituted ethylenediamine is added to a stirred suspension of IV and 10% sodium hydroxide solution. The mixture is stirred at room temperature for 3–5 h. The workup of this reaction is the same as described above, to give tertiary amide (V).

Amide (V) is reduced with LAH as follows. To a solution of tertiary amide (V) (2.0 g) in anhydrous THF is added an excess (4–5 fold) of lithium aluminum hydride. The reaction mixture is heated at reflux overnight. The reaction is quenched by the careful addition of a saturated solution of sodium potassium tartrate. After quenching, excess LAH additional water (50 mL) is added. The desired product is then is extracted in chloroform, the organic layer is separated, dried, and then volatiles are removed to generate the desired dialkylated BAT ligand (VI).

The Tc-99m complex (VII) may be prepared as follows. An aqueous solution of the hydrochloride salt of the ligand to be studied (1.0–2.0 mg/mL) is prepared. To 0.2 mL solution of the ligand is added 2.0 mCi of $Na^{99m}TcO_4$. A freshly prepared solution from a saturated aqueous stannous tartarate (0.2 mL) is then added to the mixture and incubated at room temperature for 10–15 min. A saturated solution of sodium bicarbonate (0.5 mL) is added to the mixture and $^{99m}Tc$-chelate vortexed and extracted in 1.0 mL chloroform or ethylacetate. The organic layer is separated from aqueous, evaporated under a stream of air, dissolved in methanol and purified by HPLC The desired fractions are collected and solvents removed in vacuo, and dissolved in normal saline for further studies. The complexation of N-alkylated BAT ligands or N-alkylated MAMA ligands with technetium results in the formation of syn and anti diastereomeric isomers, each as a pair of enantiomers. The stereochemistry reflects the orientation of N-alkyl group syn or anti with respect to apical oxygen. Each pair of enantiomers may be separated using HPLC methods.

A Tc-99g complex may be synthesized as follows. To a 20 mL scintillation vial is added ammonium pertechnetate (104 mg, 0.57 mmol), hydrochloride salt of the desired compound according to the invention (1.2 eq.) and 50% aqueous ethanol (10 mL). The mixture is stirred at room temperature and solid stannous tartarate (154 mg) is added. The contents are stirred at room temperature for overnight whereby color of solvent changes.

EXAMPLE 2

Synthesis of MAMA Ligands

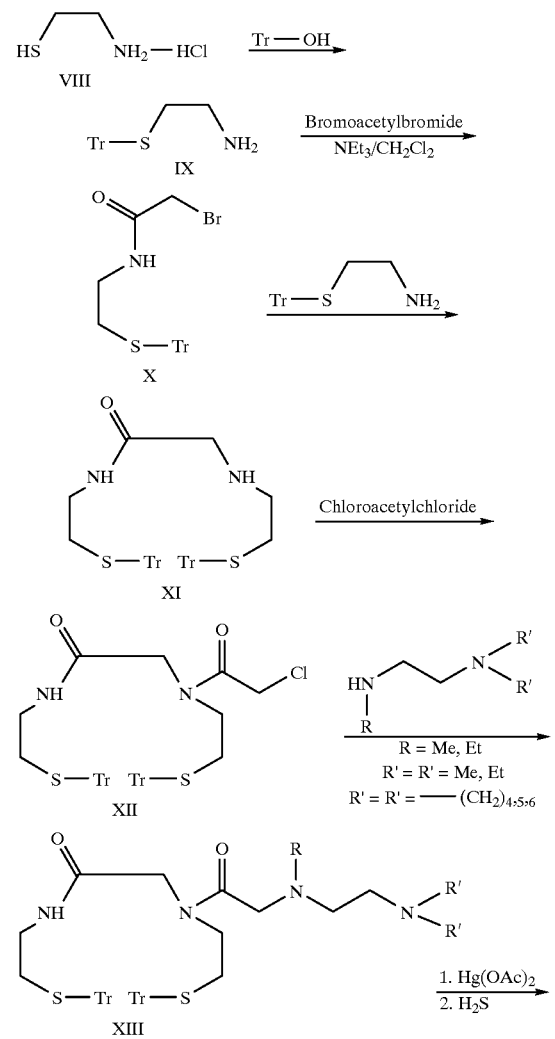

-continued

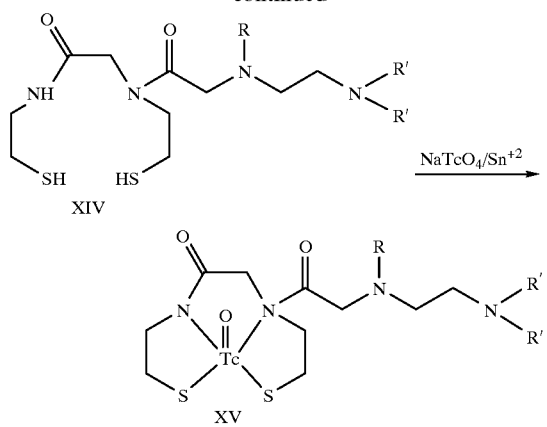

A further exemplary procedure for synthesis of compounds of the formula $K_1$ is shown in Example 2. A literature procedure has been used to prepare the basic compound, which may be monoamino-monoamide dithiol (MAMA) or derivatives thereof. See O'Neil, J. P. et al. Inorg. Chem. 33, 319–323, 1994, which is hereby incorporated by reference. The synthesis of such MAMA derivatives is shown in Example 2.

The first step was synthesis of S-(Triphenylmethyl)-2-aminoethanethiol. This was accomplished as follows. To a solution of cystamine (VIII) (11.36 g. 0.1 mol) in trifluoroacetic acid (116 ml, 1.5 mol) at room temperature was added triphenylmethanol (26.0 g, 0.1 mol). After stirring for one hour, the mixture was reduced under reduced pressure, and diluted with ethylacetate (100 ml). The mixture was washed with 3 N aqueous NaOH (3×50 ml). The organic layer was separated, dried over anhydrous sodium sulfate. The organic layer was reduced in volume and put in a freezer to give the desired trityl protected amine (IX).

N-(2-Bromoacetyl)-S-(triphenylmethyl)-2-aminoethanethiol, (X) was prepared as follows. To a stirred solution of bromoacetylbromide (1.09 ml, 12.5 mmol) in dry methylene chloride was added dropwise over 15 min at —40° C a solution of trityl protected aminoethanethiol IX (4.0 g, 12.5 mmol). The mixture was allowed to warm up to room temperature and stirred for 15 min. The mixture was quenched with water (50 ml). The organic layer was separated, and washed with 1 N HCl and then with aqueous $NaHCO_3$. The organic layer was reduced in volume (35 ml) and hexanes (100 ml) were added to give white crystals of the target compound, (X).

N-[2-((2-((Triphenylmethyl)thio)ethyl)amino)acetyl]-S-(triphenylmethyl)-2-aminoethanethiol, (XI) (MAMA) was then prepared. To a solution of above bromide (4.27 g, 9.70 mmol) and triethylamine (2 ml, 14.3 mmol) in $CH_2Cl_2$ (30 ml) was added amine (3.1 g, 9.7 mmol) as a suspension in $CH_2Cl_2$ (15 ml). The mixture was stirred at room temperature for 24 h, and then quenched with water (50 ml). The organic layer was separated, dried over anhyd. sodium sulfate, concentrated and followed by column chromatography to provide target MAMA.

Continuing, the next step in the synthesis was preparation of N-[2-(chloraecetyl)(2-((triphenylmethyl)thio)ethyl) amino)]acetyl-S-(triphenylmethyl)-2-aminoethanethiol (XII). To an ice-cold solution of MAMA (4.2 g, 6.2 mmol), (XI), in $CH_2Cl_2$ (100 mL) ad 10% aqueous sodium hydroxide (50 mL) was added a solution of chloroacetylchloride (0.71 mL, 8.9 mmol). The mixture was stirred for 1 h at 0° C. and 50 mL of cold water was added. The organic layer was separated, washed with sodium bicarbonate solution and dried over anhydrous sodium sulfate. The volatiles were removed in vacuo, (XII).

This product was then used in the preparation of N-[2-((substituted ethylenediamine)(2-((triphenylmethyl)thio) ethyl)amino)]acetyl-S-(triphenylmethyl)-2-aminoethanethiol, (XIII). The chloro compound (1.0 g) obtained from the above reaction was dissolved in $CH_2Cl_2$ (50 ml). To this was added triethylamine (3.0 ml) and N-methyl-N',N'-dialkylethylamine (1 eq). The mixture was stirred at room temperature overnight. The organic layer was separated from aqueous layer, dried, and the volatiles were removed in vacuo. The desired compound, (XIII), was purified by column chromatography.

This compound was then used in the preparation of N-[2-((substituted ethylenediamine)(2-mercaptoethyl) amino)]acetyl-2-aminoethanethiol, (XIV). To a stirred solution of (XIII) (0.1 mmol) in a 1:1 mixture of EtOH and EtOAc (5 mL) was added a solution of mercury(II)acetate (0.3 mmol) in EtOH (2 mL). The mixture was heated at reflux for 30 min, and cooled to room temperature. Gaseous $H_2S$ was bubbled through the solution until the mixture became completely black. The mixture was stirred for an additional 15 min and passed through a pad of Celite with EtOAc (30 mL). The volatiles were removed in vacuo and, if necessary, the desired MAMA ligand, (XIV), was purified using a short plug silica gel. Compound (XIV) was suitable for forming complex (XV).

EXAMPLE 3

Synthesis of MAG-3 Conjugates

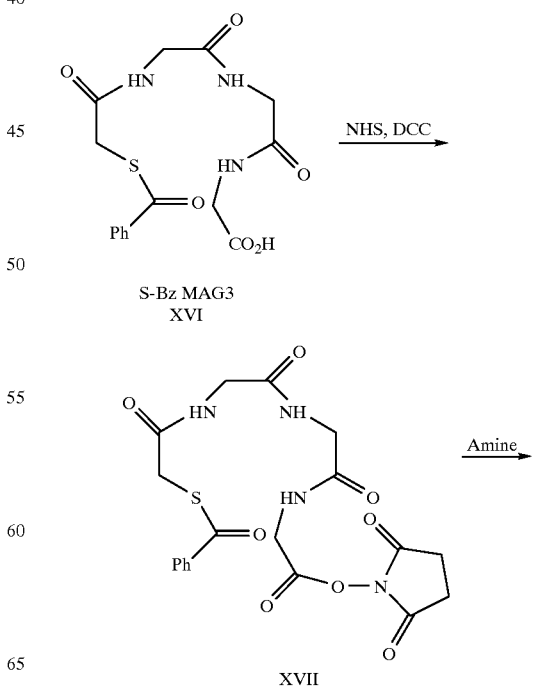

-continued

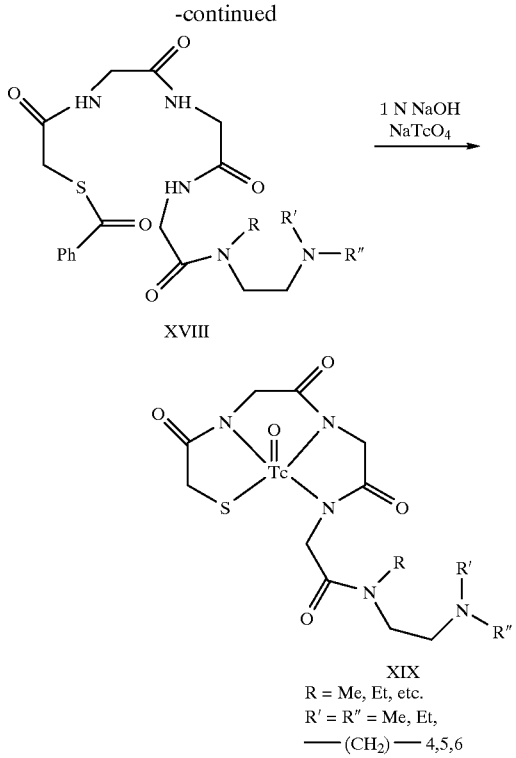

XVIII

XIX
R = Me, Et, etc.
R' = R" = Me, Et,
—(CH$_2$)—4,5,6

A further exemplary procedure for synthesis of compounds of the formula K$_1$ was as follows. MAG-3 ligand, (XVI), was synthesized using literature procedures (Fritzberg et al. 1986, hereby incorporated by reference). Next, one equivalent of MAG-3 was reacted with 1.1 eq of N-hydroxysuccinimide (NHS) and 1,3-dicyclohexyldicarbodiimide (DCC) in DMF at room temperature for 4 h. The dicyclohexylurea was filtered, and solvents were removed in vacuo and the activated ester purified using a chromotographic method. This active ester (XVII) was conjugated to a variety of amines by stirring active ester with equivalent amount of amine at room temperature for 3–4 h to give the desired MAG-3 conjugates with appended sigma receptor pharmacophores (XVIII). This synthesis is shown above. Compound (XVIII) can be used to form complex (XIX), as shown.

EXAMPLE 4

Compounds of the formula K$_2$ were synthesized as follows. The chelating moiety were prepared according to literature methods. M. J. Abrams et al., J. Nucl. Med., 31:2022–2028 (1990), which is hereby incorporated by reference. The chelating moiety was alkylated using the methods generally outlined above which results in the appending of the pharmacophore moiety to the chelating moiety.

EXAMPLE 5

Exemplary procedures for synthesis of complexes according to the invention begin with obtaining compounds according to the invention, as discussed generally above. Preparation of Tc-99m complexes using the compounds according to the invention occurred as follows. An aqueous solution of the hydrochloride salt of the ligand of interest (1.0–2.0 mg/mL) was prepared. To 0.2 mL solution of the ligand, was added 2.0 mCi of Na$^{99m}$TcO$_4$. A freshly prepared solution from a saturated aqueous stannous tartarate (0.2 mL) was then added to the mixture and incubated at room temperature for 10–15 min. A saturated solution of sodium bicarbonate (0.5 mL) was added to the mixture and $^{99m}$Tc-chelate vortexed and extracted in 1.0 mL chloroform or ethylacetate. The organic layer was separated from aqueous, evaporated under a stream of air, dissolved in methanol and purified by HPLC. The desired fractions were collected and solvents removed in vacuo, and dissolved in normal saline for further studies. The complexation of N-alkylated BAT ligands or N-alkylated MAMA ligands with technetium resulted in the formation of syn and anti-diastereomeric isomers, each as a pair of enantiomers. The stereochemistry reflects the orientation of N-alkyl group syn or anti with respect to apical oxygen. Each pair of enantiomers were separated, as necessary, using HPLC methods.

MAG-3 based chelates were labeled, as necessary, with Tc-99m by the hydrolysis of the benzoyl protecting group on the sulfur atom using a mild base (e.g. 0.5 N NaOH or NaHCO$_3$). Addition of sodium pertechnetate to the resulting thiol compound in the presence of stannous chloride resulted in the desired Tc-99m chelate.

Tc-99g complexes of the compounds according to the invention were synthesized as follows. To a 20 mL scintillation vial was added ammonium pertechnetate (104 mg, 0.57 mmol), hydrochloride salt of the desired compound according to the invention (1.2 eq.) and 50% aqueous ethanol (10 mL). The mixture was stirred at room temperature and solid stannous tartarate (154 mg) is added. The contents were stirred at room temperature overnight and the color of the solvent changed.

EXAMPLE 6

All chemicals and reagents not otherwise noted were purchased from Aldrich Chemical Company. Melting points were determined with a Fisher-Johns apparatus and are reported uncorrected. $^1$H NMR spectra were recorded on a Bruker 300 AM spectrometer. The thin-layer chromatography (TLC) system consisted of Analtech uniplate silica gel GF plates (250 micron, 10×20 cm). Mass spectra (chemical ionization or electron impact) were recorded on a Finnigan 1015 mass spectrometer. For Tc-99g complex, electrospray ionization (ESI) mass spectra was obtained using the Finnigan TSQ700 triple quadrupole mass spectrometer. Na$^{99m}$TcO$_4$ was eluted using a Mo-99/Tc-99m generator obtained from DuPont Merck, Billerica, Mass. Elemental analysis was performed by Quantitative Technologies, Inc., Whitehouse, N.J. Imidazolidinol[1,2-d]dithiazepine

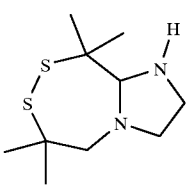

I was prepared according to published method of A. V. Joshua, et al., Transannular cyclizations of 1,2-dithia-5,8-diazacyclodeca-4,8-dienes during borohydride reduction., J. Org. Chem. 52:2447–2451 (1987), hereby incorporated by reference.

Acylation of Imidazolidino[1,2-d]dithiazepine with chloroacetyl chloride: 10% NaOH (50 mL) was added to a solution of imidazolidino[1,2-d]dithiazepine (8.6 g, 37 mmol) in CHCl₃ (50 mL); the resulting mixture was then cooled with an ice-water bath. To this, chloroacetyl chloride (4.2 mL, 53.3 mmol) was added and stirred for an hour. The bath was removed and stirred for an additional 0.5 hr. The organic layer was separated, dried over anhydrous sodium sulfate, and evaporated to a thick oil. This oil was dissolved in ethyl acetate:hexanes (1:5) to give a white solid (5.2 g, 45%) of the following structure.

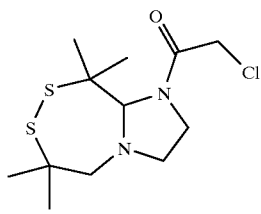

XX

¹H NMR(CDCl₃) d 1.23 (s, 3H), 1.24 (s, 3H),1.27 (s, 3H), 1.34 (s, 3H), 2.58 (d, J=15 Hz, 1H), 2.83–2.87(m, 1H), 3.24 (m, 1H), 3.32 (d, J=15 Hz, 1H), 3.45–3.55 (m, 1H), 3.70–3.76 (m, 1 H), 4.04 (s, 2H), 4.71 (s, 1H). Anal. Calcd for $C_{12}H_{21}N_2OS_2Cl$. C; 46.66, H; 6.85, N; 9.07; Found: C; 46.75, H; 6.68, N; 9.03.

Alkylation of (XX) with N-methyl-2-(1-piperidinyl) ethylamine: To a solution of the compound of formula XX (6.0 g, 20 mmol) in dry DMF (50 mL), powdered potassium carbonate (3.3 g, 23.9 mmol) was added. To this N-methyl-2-(1piperidinyl)ethylamine (4.26 g, 29.9 mmol) was added and stirred overnight at room temperature. This was evaporated to dryness under vacuum, and then washed with water (2×50 mL). This was redissolved in chloroform, washed with water, and dried over anhydrous sodium sulfate. The organic layer was evaporated to dryness. This oil was converted to hydrochloride salt and recrystallized from 20% ethanol in acetonitrile to give quantitative yields of a compound of formula (XXI).

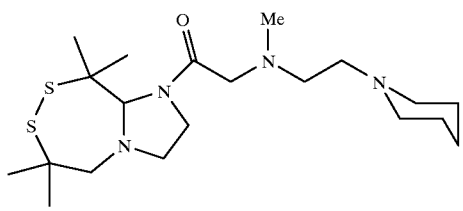

XXI

¹H NMR (CDCl₃) 1.17–1.26 (m, 12H), 1.33–1.49 (m, 6H), 2.21 (s, 3H), 2.3–2.5 (m, 9H), 2.5–2.7 (m, 1H), 2.9–3.1 (m, 2H), 3.2–3.3 (m, 3H), 3.9–4.0 (m, 1H), 4.65 (s, 1H). Anal. Calcd. for $C_{20}H_{38}N_4OS_2$. C; 57.93, H; 9.24, N; 13.51, Found C; 58.05, H; 9.12, N; 13.39.

Reduction of (XXI) with LAH: To the suspension of LAH (2.2 g) in THF (100 mL), a solution of amide (4.0 g) was added and heated at reflux for 19 h. The reaction mixture was quenched with saturated aqueous NH₄Cl. Ether (50 mL) was then added and filtered through a pad of celite. The solid was washed with ether (3×50 mL) and ethanol saturated with HCl was added to the combined ether to give a sticky white solid of formula (XXII).

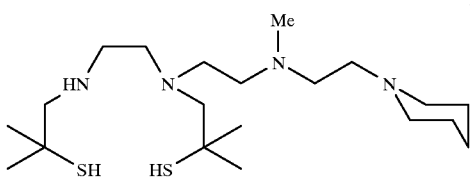

XXII

To this more ethanol was added to give powdery white solid (2.0 g, 38%). m/e=405 [M+I]⁺. This reduction reaction gave the desired ligand, which possessed free bisaminothiol groups for chelating Tc-99m along with the pendant recognition elements for sigma receptor affinity.

EXAMPLE 7

A Tc-99m[EN-6] complex was prepared as follows. An aqueous solution of the ligand of formula (XXII)

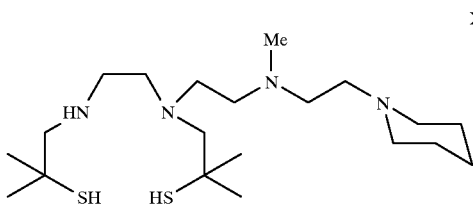

XXII (1.0 mg/mL) was prepared. To 0.2 mL solution of the ligand was added 2.0 mCi of Na$^{99m}$TcO₄. A freshly prepared solution from a saturated aqueous stannous tartarate (0.2 mL) was added to the mixture and incubated at room temperature for 10 min. A saturated solution of sodium bicarbonate (0.2 mL) was added to the mixture. The $^{99m}$Tc [EN-6] mixture was vortexed and extracted in 1.0 mL chloroform. The organic layer was separated from the aqueous layer, evaporated under a stream of air, dissolved in methanol and purified by HPLC. The labeling of BAT ligand with Tc-99m was carried out in high yields (>80%) using stannous tartarate as a reducing agent resulting in the target sigma [Tc-99m]EN6, (XXIII).

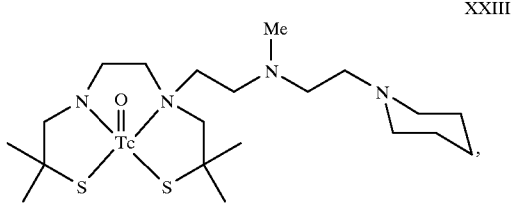

XXIII

[Tc-99m]EN6

The lipid soluble $^{99m}$Tc-complex (XXIII) [Tc-99m]EN6 was extracted from the aqueous solution using chloroform and purified by using C-18 reversed phase HPLC column [retention time=15 min, 90/10: methanol/tris-hydrochloride (10 mM, pH=4.5) buffer]. It is well known for BAT ligands that they form a square pyramidal technetium (V)-oxo core with the oxo group occupying the apical position. The complexation of N-monoalkylated BAT ligands with technetium results in the formation of syn and anti diastereomeric isomers each as a pair of enantiomers. The stereochemistry reflects the orientation of the N-alkyl group syn or anti with respect to apical oxygen. J. P. DiZio, et al., Progestin-rhenium complexes: metal-labeled steroids with high receptor binding affinity, potential receptor-directed agents for diagnostic imaging or therapy, Bioconjugate Chem. 2:353–366 (1991); A. Mahmood, et al., Stereoisomers of neutral oxotechnetium(V) and oxorhenium (V) complexes, 3 Technetium in Chemistry and Nuclear Medicine 119–23 (M. Nicolini, G. Bandoli, and U. Mazzi, Eds., Cortina International, Verona, Publ.) (1990), all of which are hereby incorporated by reference. A HPLC trace of Tc-99m complex indicated two peaks related to syn and anti isomers in an approximate ratio of 55/45 respectively.

The desired fractions were collected and solvents removed in vacuo, and then dissolved in normal saline for cell binding studies. The yields were 80–95%.

EXAMPLE 8

The Tc-99g[EN-6] ground state complex was prepared as follows. To a 20 mL scintillation vial was added ammonium pertechnetate (104 mg, 0.57 mmol), 273 mg (0.59 mmol) hydrochloride salt of the ligand of formula (XXII)

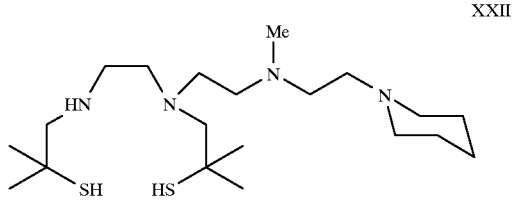

XXII and 50% aqueous ethanol (10 mL). The mixture was stirred at room temperature and, as a reducing agent, solid stannous tartarate (154 mg) was added. The contents were stirred overnight at room temperature whereupon the solvent became a light brown color. The complex was extracted from the solvent by addition of (2×1 mL) chloroform. The organic layers were combined and evaporated overnight in a hood and the Tc-99g[EN-6] complex was purified by passing through a silica gel column eluting with $CHCl_3$/MeOH: 90/10. m/z=517 (MH$^+$).

As expected, a neutral, lipophilic TcO(V) complex was obtained, characterized by electrospray ionization mass spectroscopy (MH$^+$=517). The mass spectral fragmentation {a loss of (S—C(CH$_3$)$_2$CH$_2$) (m/z=429)} was also consistent with the chemical structure. The HPLC retention time for both Tc-99m and Tc-99g were identical under identical conditions indicating the formation of the same species at carrier free and the ground state radionuclide.

EXAMPLE 9

T47D human ductal breast carcinoma cells were purchased from ATCC, Rockville, Md. and cultured in serum supplemented medium DMEM containing 10% heat inactivated fetal bovine serum (GIBCO) at 37° C. The cells were adherent and split weekly in a 1:20 ratio using trypsin/EDTA (GIBCO). The cells were then transferred to 24 well plates and allowed to be adherent and confluent (about 0.5 million cells) or the cells were grown in T75 cell culture flasks and were detached when they were confluent using trypsin/EDTA (0.025%) or scraped with a cell scraper in DMEM.

In-vitro sigma receptor binding assays were carried out using guinea pig brain membranes according to art-recognized procedures with some modifications. W. D. Bowen et al., Pentazocine: A potent and highly selective benzamorphan-based probe for sigma-1 receptors, Mol. Neuropharmacol. 3:117–126 (1993); B. R. de Costa et al., Synthesis and evaluation of optically pure [$^3$H](+)-pentazocine, a highly potent and selective radioligand for sigma receptors, FEBS Letters 251:53–58 (1989), all of which are hereby incorporated by reference. Guinea pig brain membranes (500 ug of proteins) were incubated with 5 nM [$^3$H]DTG (39.4 Ci/mmol) and various concentrations of competing ligand in 0.5 ml Tris-HCl pH 8.0 for 120 min at 25° C. Non-specific binding was determined in the presence of 10 uM haloperidol. [Tc-99g]EN6 was used in 12 concentrations ranging from 0.05–10,000 nM. Assays were terminated by dilution with 5 ml ice-cold 10 mM Tris-HCl pH 8.0 and the solution was filtered through glass fiber filters using a Brandel cell harvester (Brandel, Gaithersburg, Md.). Filters were then washed twice with ice-cold buffer. Filters were soaked in 0.5% polyethyleneimine for at least 30 min at 25° C. prior to use. The filters were then counted in CytoScint (ICN, Cosa Mesa, Calif.) after an overnight extraction of counts. In order to control for possible interference with tritium beta counting from Tc-99g beta emission, parallel curves were run under exactly the same conditions using membranes and 0.05–10,000 nM [Tc-99g] EN6, except with the omission of [$^3$H]DTG. No radioactivity above background could be detected in tritium channel at [Tc-99g]EN6 concentrations up to 1,000 nM, thus no correction was necessary. IC$_{50}$ values were determined using the computerized iterative curve-fitting program GraphPAD Inplot4 (Graphpad software, San Diego, Calif.).

The receptor binding specificity of Tc-99m complex (XXIII)

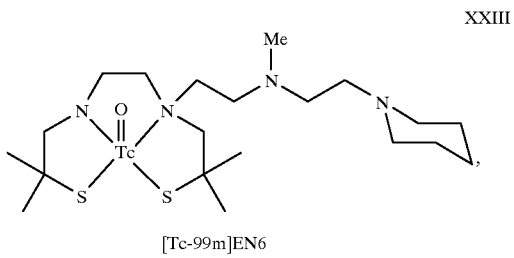

XXIII

[Tc-99m]EN6 was determined by its binding to human ductal breast cancer (T47D) cells, possessing a high density of both sigma-1 and sigma-2 sites. A high degree of specific binding (90–97%) of the Tc-99m complex was obtained when sigma receptor ligands such as halogenated phenylethylenediamines (BD1008 and IPEMP) were used to determine non-specific binding. A modest affinity dose dependent inhibition of binding was found with BD1008 and IPEMP (IC$_{50}$=47±2 and 59±5 nM, respectively), known sigma ligands. No specific binding was found with Tc-99m chelate without appended sigma pharmacophore (N-alkyl substituted ethylenediamine) showing that biological activity resulted from the pendant pharmacophore.

EXAMPLE 10

Competition binding studies in human ductal breast cancer cells (T47D) were performed as follows. T47D cells were cultured in serum supplemented medium (RPMI-1640)

containing 10% heat inactivated fetal bovine serum (GIBCO) at 37° C. The cells were adherent and split weekly in a 1:20 ratio using trypsin/EDTA (GIBCO). The cells were scraped using a cell scraper from T75 culture flasks and centrifuged in a Sorvall 6000B centrifuge at a speed of 4000 rpm. The growth medium was removed and the cell pellet was resuspended in RPMI 1600 serum free media.

The affinity of compounds for sites labeled by [Tc-99m] EN6 in human breast cancer cells was determined by heterologous in-vitro competitive binding assays in whole cells. The following method was used: A small aliquot of the cell suspension (100 μL) was incubated with [Tc-99m]EN6 and varying concentrations to ($10^{-4}$ to $10^{-12}$ M) of arylethylenediamines keeping a total volume 1.0 mL constant. The cells were incubated at 37° C. for 1 hr and subsequently filtered through a Brandel Cell harvester (Brandel, Gaithersburg, Md.) and washed with de-ionized cold water. The radioactivity associated with the cells on filters was counted on a Beckman (DP 5500) Gamma Counter. The optimum pH for the binding was found to be between 7–8.

The data was analyzed with the iterative nonlinear least square curve fitting program GraphPAD Inplot (Graph PAD Software, San Diego, Calif.). The Cheng-Prussoff equation was then used to convert $IC_{50}$ values to apparent $K_1$ values.

The chelate's binding specificity for sigma receptors was explored in T47D cells using two high affinity sigma ligands, BD1008 and IPEMP, in competition experiments. BD1008 and IPEMP displayed a $K_i$=2.1±0.8 nM and 0.82±0.13 nM, respectively for sigma-1 sites in guinea pig brain against [$^3$H]-(+)-pentazocine and Ki=8.1±2.2 nM and 15.2±2.35 nM, respectively for sigma-2 sites in rat liver membrane preparation against [$^3$H]DTG in the presence of dextrallorphan. A dose-dependent inhibition of binding of Tc-99m complex XXIII was observed using BD1008 and IPEMP ligands ($IC_{50}$=47±2 nM and 59=5 nM respectively), indicating that it is labeling sigma receptors. Results from this experiment are shown in FIG. 1.

To further explore binding affinity of the Tc-99m chelate, the binding studies of Tc-99g complex were studied in guinea pig brain membranes against [$^3$H]DTG (a known sigma ligand). A high affinity dose dependent inhibition of binding of [$^3$H]DTG was found in the presence of Tc-99g complex, indicating the binding at sigma sites. Ki value for Tc-99 complex was found to be 42.7±8.57 nM. This represented a combined binding affinity for sigma-1 and sigma-2 subtypes as [$^3$H]DTG is a sigma non-subtype selective ligand. It should be noted however, that there was no specific binding of Tc-99 complex without the pendant pharmacophore confirming that binding activity resulted from the pendant ethylenediamine moiety and indicating that the binding was to sigma sites. No specific binding was found with Tc-99m chelate without substituted ethylenediamine pharmacophore.

EXAMPLE 11

Saturation binding and Scatchard's analysis of [Tc-99m] EN6, XXIII, were carried out in membranes from T47D human ductal breast cells, which were prepared as described previously. A methanol/sodium phosphate buffer, pH 8.0, solution of carrier-free [Tc-99m]EN6 in trace concentration was mixed in equal proportion with a 10 uM solution of [Tc-99g]EN6 to approximately 0.35 Ci/mmol. This solution was diluted into glass or polypropylene assay tubes to final concentrations ranging from 1 nM–1,000 nM. Incubations were carried out in a final volume of 0.25 mL of 50 mM Tris-HCl containing 250 ug of membrane protein for 120 min at 37° C. Non-specific binding was determined at each radioligand concentration in the presence of 10 uM BD1008, a ligand with high affinity for both sigma-1 and sigma-2 receptors. Assays were terminated by addition of 0.5 ml of ice cold 10 mM Tris-HCl, pH 8.0 and filtration through glass-fiber filters. Filters were then washed twice with 0.5 ml of ice cold buffer and counted in a gamma counter.

Filters were soaked in 0.5% polyethyleneimine for at least 30 min prior to use in order to reduce non-specific binding of radioligand to filters. Each experiment was carried out in duplicate. Data was analyzed using the iterative curve-fitting program BDATA (Baltimore, Md.).

Figure 2:
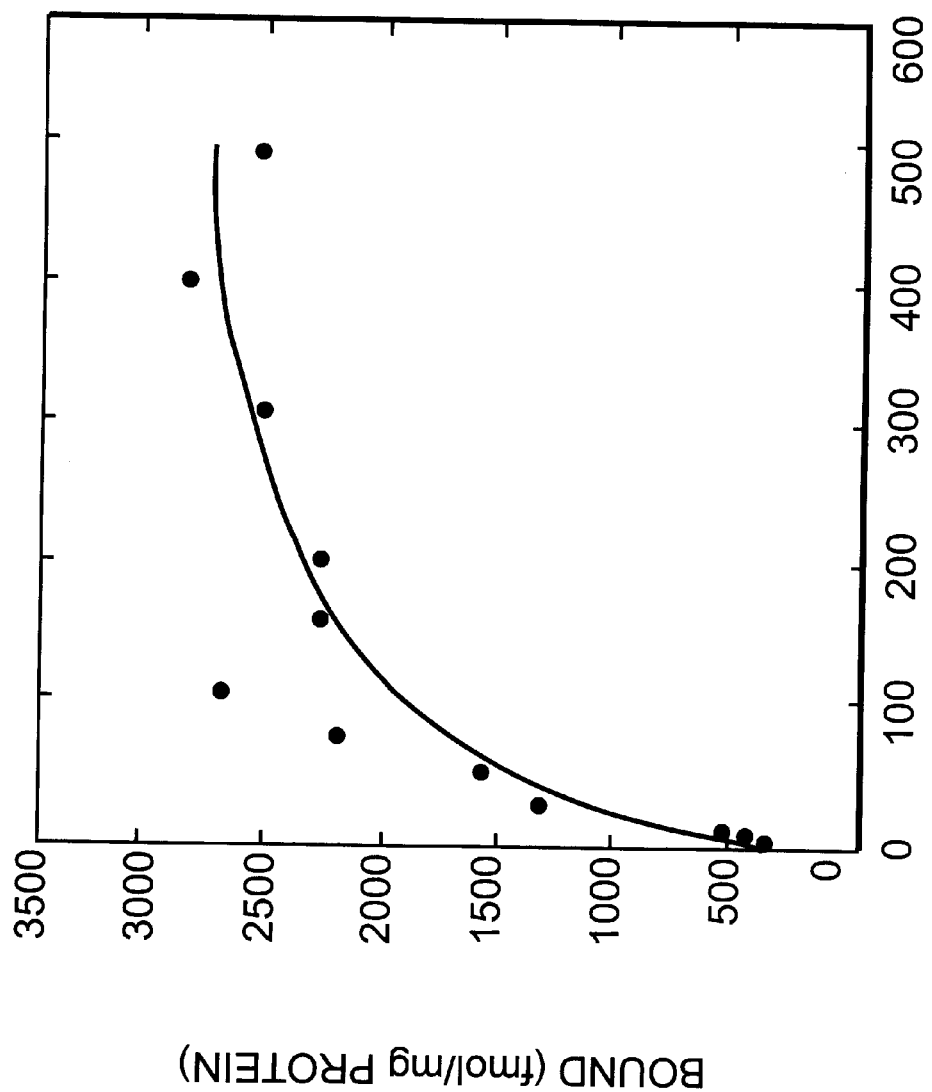
FIG. 2 is a saturation plot of [Tc-99m]EN6 binding in T47D breast cancer cell membranes.
Figure 3:
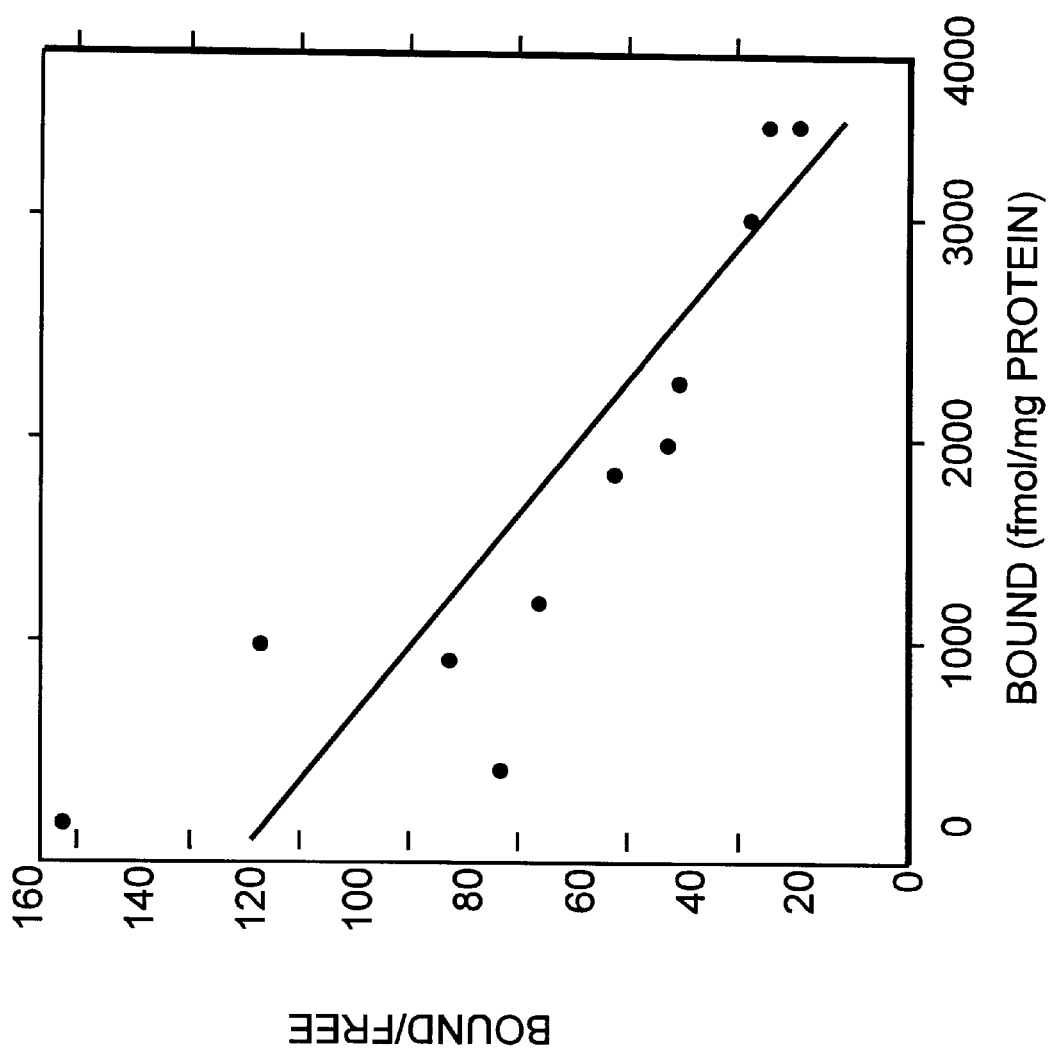
FIG. 3 is a Scatchard's plot of [Tc-99m]EN6 binding in T47D breast cancer cell membranes.

The saturation binding of [Tc-99m]EN6, XXIII, in membrane preparations of T47D cells was studied using Scatchard's analysis. The incubation of an increasing concentration of HPLC purified [Tc-99m]EN6 chelate {spiked with a known concentration of [Tc-99g]EN6} showed a saturable binding, with $K_d$=43.5±114.7 nM and a B max of 31211130 fmol/mg of protein. FIGS. 2 and 3 show the results from this experiment in a saturation plot and a Scatchard's plot. The binding saturates with increasing concentration of the tracer and a high Bmax was found. This result is consistent with our earlier findings where we had shown that a high density of sigma receptors (3000–3500 fmol/mg of protein) were expressed in T47D cells based upon [H-3]DTG binding in T47D cell membranes.

EXAMPLE 12

Animal biodistribution and blocking studies were performed in rats as follows. Sprague Dawley rats (200–250 g) were anesthetized with ketamine/xylazine and injected intravenously with $^{99m}$Tc-EN6, XXIII, (10–20 ÂCi) in 0.2 ml saline containing up to 20% ethanol solution. At 0.5, 1, and 4 hr post-injection blood samples were drawn by cardiac puncture and the rats were sacrificed thereafter by cardiectomy while under ketamine/xylazine anesthesia. The organs of interest were then excised, blotted with tissue paper, weighed and the radioactivity counted. The % injected dose/organ was determined by comparison of the tissue radioactivity with suitably diluted, known quantity aliquots of the injected dose. For in-vivo blocking studies, 2.16 micromol of BD1008 was pre-mixed with $^{99m}$TcEN6 and then injected through the tail vein. The animals were sacrificed at 4 hr post-injection and the organs of interest were removed and handled as above.

The biodistribution of $^{99m}$Tc-EN6 in Sprague-Dawley rats (Table I) showed a hepatobiliary excretion, as expected. The tracer cleared quickly from the blood pool and was extracted in high amounts by liver (19.31% ID/organ at 30 min and 21.91% ID/organ at 4 hr post-injection). A good uptake of the tracer was also found in lungs and kidneys. The evidence for in-vivo receptor binding was established by in-vivo blocking of specific binding with BD1008. The uptake of the radiopharmaceutical at 4 hr post i.v. injection was 2.49%

ID/organ in the kidney whereas uptake in the presence of 2 micromol BD1008 was 1.03% D/organ (Table 1).

TABLE I

Tissue Distribution of $^{99m}$Tc[EN6] in Sprague-Dawley Rats (% ID/organ ± S.D.; n = 4)

| Tissue | 0.5 Hr | 1.0 Hr | 4.0 Hr | 4.0 Hr w/BD1008 2.16 μmol |
|---|---|---|---|---|
| Blood | 4.38 ± 1.33 | 3.66 ± 0.87 | 1.62 ± 0.23 | 0.77 ± 0.03 |
| Heart | 0.31 ± 0.03 | 0.24 ± 0.03 | 0.15 ± 0.01 | 0.07 ± 0.01 |
| Liver | 19.11 ± 2.01 | 15.55 ± 0.17 | 21.91 ± 2.37 | 14.46 ± 1.21 |
| Lung | 2.64 ± 0.27 | 1.07 ± 0.16 | 0.90 ± 0.10 | 0.47 ± 0.09 |
| Kidney | 3.62 ± 0.33 | 3.48 ± 0.34 | 2.49 ± 0.28 | 1.03 ± 0.13 |
| Spleen | 0.87 ± 0.08 | 0.66 ± 0.06 | 0.52 ± 0.06 | 0.25 ± 0.07 |
| Stomach | 4.64 ± 0.30 | 1.60 ± 0.19 | 2.81 ± 0.60 | 7.13 ± 2.07 |
| Muscle | 21.74 ± 1.80 | 9.01 ± 0.74 | 13.05 ± 5.23 | 6.08 ± 1.21 |
| Brain | 0.06 ± 0.01 | 0.03 ± 0.01 | 0.03 ± 0.01 | 0.02 ± 0.00 |

Thus, a co-injection of $^{99m}$Tc-complex along with 2 micromol BD1008 in male Sprague-Dawley rats resulted in an inhibition of binding of about 60% at 4 hr post-i.v. injection in the kidneys, an organ that is known to possess high densities of both sigma-1 and sigma-2 receptors. S. B. Hellewell, et al., Rat liver and kidney contain high densities of sigma-1 and sigma-2 receptors: characterization by ligand binding and photoaffinity labeling, Eur. J. Pharmacol.—Mol. Pharmacol. Sect. 268:9–18 (1994), all of which are hereby incorporated by reference. Similarly, a significant reduction of radioactivity was also found in liver (34%) and lungs (48%) at 4 hr post-injection.

What is claimed is:

1. A compound, for use in radioimaging and radiotherapy, of the formula $K_1$

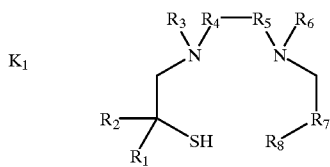

wherein $R_1$ and $R_2$ are H or Me;

$R_3$ is H, lower alkyl, lower alkylene, cycloalkyenyl, aryl, or arylalkane;

$R_4$ and $R_5$ are independently

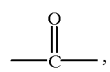

—CH$_2$—, or

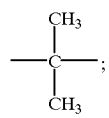

$R_6$ is —(CH$_2$)$_j$—CZ—NR$_{10}$—(CH$_2$)$_m$—R$_9$;

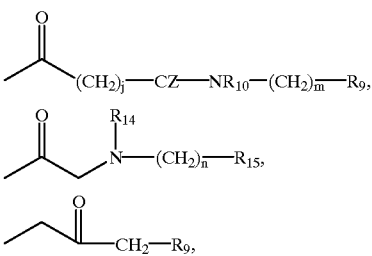

or hydrogen;

$R_7$ is

—CH$_2$—, or

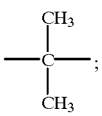

$R_8$ is —SH, or

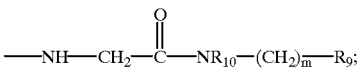

$R_9$ and $R_{15}$ are —N(R$_{10}$)$_2$ or a 5 to 7 membered heterocyclic ring, containing nitrogen, oxygen, or sulfur, the ring being unsubstituted or optionally substituted wi least one alkyl or arylalkyl substitutent, said heterocyclic ring containing 2–6 ring ca atoms and 1–3 ring heteroatoms;

$R_{10}$ and $R_{14}$ are independently lower alkyl or hydrogen;

$R_{11}$ is hydrogen or methyl;

Z is oxygen or 2 hydrogen atoms;

m is an integer from 0 to 6;

n is an integer from 1 to 6;

and j is an integer from 0 to 6;

wherein if $R_6$ is hydrogen, then $R_8$ is not —SH; and if $R_9$ is —N(R$_{10}$)$_2$ or said 5 to 7 membered heterocyclic ring is linked to the —(CH2)$m$— moiety by a heteroatom, then m is not 0.

2. A compound as claimed in claim 1, wherein the compound is

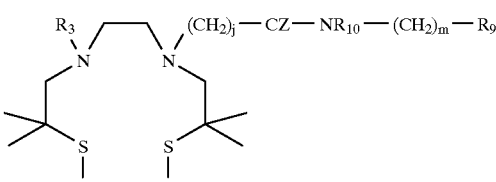

wherein Z, j, m, R$_3$, R$_9$, and R$_{10}$ are as defined above, and R$_7$ is —C(CH$_3$)$_2$—.

3. A compound as claimed in claim 1, wherein the compound is

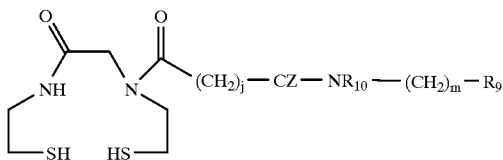

wherein Z, j, m, $R_9$ and $R_{10}$ are as defined above.

4. A compound as claimed in claim 1, wherein the compound is

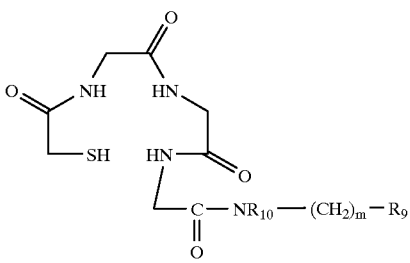

wherein j, m, $R_9$, and $R_{10}$ are as defined above.

5. A compound as claimed in claim 1, wherein the compound is

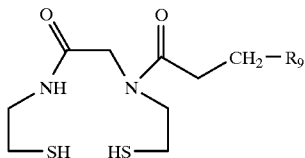

wherein $R_9$ is as defined above.

6. The compound of claim 1 wherein $R_9$ is —$N(R_{10})_2$ and each $R_{10}$ is independently lower alkyl or hydrogen.

7. The compound of claim 1 wherein $R_9$ is an N-linked 5 to 7 membered heterocyclic ring containing nitrogen which can have at least one alkyl substituent, said alkyl containing 1–6 carbon atoms, and said heterocyclic ring nitrogen including 2–6 ring carbon atoms and 1–3 ring heteroatoms of which at least one is nitrogen.

8. The compound of claim 7 wherein said heterocyclic ring is

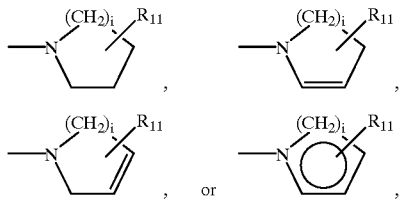

wherein i is an integer from 1 to 3 and $R_{11}$ is hydrogen or lower alkyl.

9. The compound of claim 8 wherein said heterocyclic ring is N-piperidinyl, N-pyrrolidinyl, N-pyridinyl, N-morpholinyl, N-pyrrolyl, or N-homopiperidinyl.

10. The compound of claim 1 wherein said heterocyclic ring is:

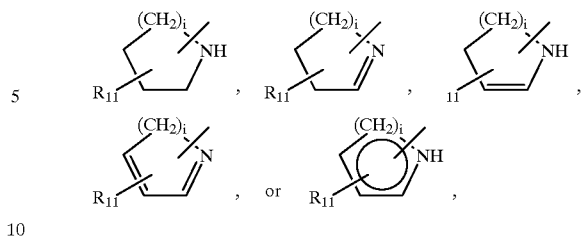

wherein i is an integer from 1 to 3 and $R_{11}$ is hydrogen or lower alkyl.

11. The compound of claim 10 wherein said heterocyclic ring is piperidenyl, pyrrolidinyl, pyridinyl, morpholinyl, homopiperidinyl or pyrrolyl.

12. The compound of claim 1, wherein each $R_{10}$ is lower alkyl.

13. The compound of claim 1, wherein each $R_{10}$ is hydrogen.

14. The compound of claim 1, wherein j=2.

15. The compound of claim 1, wherein j=0.

16. A compound according to claim 1, wherein $R_6$ is selected from:

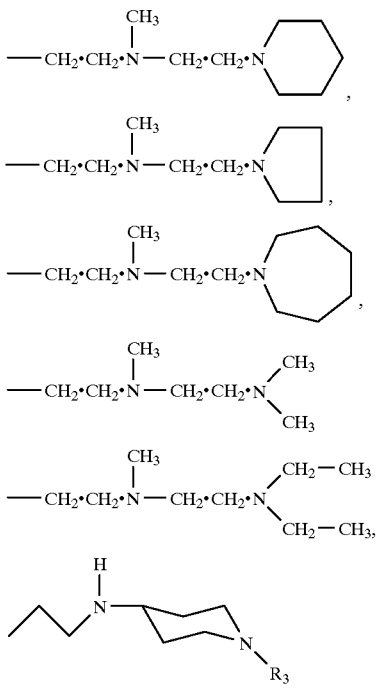

wherein $R_3$ is as defined above.

17. A compound according to claim 1 wherein the compound is:

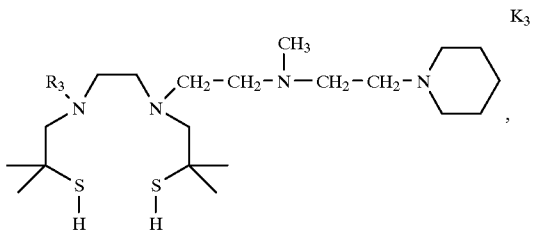

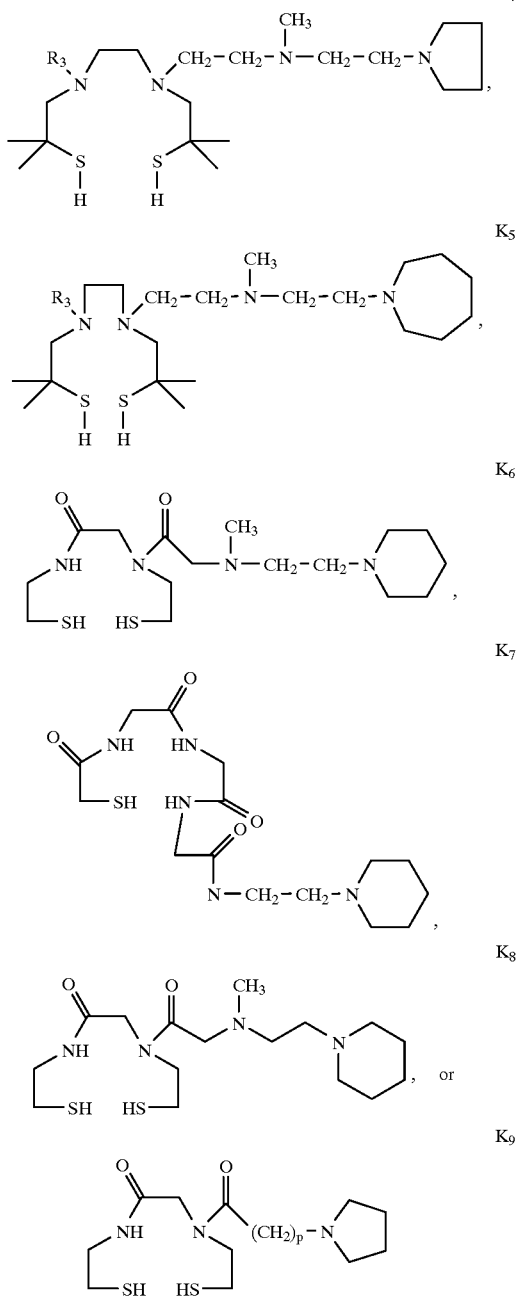

wherein $R_3$ and $R_{10}$ are as defined above and p=is an integer from 1 to 6.

18. A complex comprising the compound of claim 1 and $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$.

19. A complex comprising the compound of claim 2 and $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$.

20. A complex comprising the compound of claim 3 and $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$.

21. A complex comprising the compound of claim 4 and $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$.

22. A complex comprising the compound of claim 5 and $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$.

23. A complex comprising the compound of claim 6 and $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$.

24. A complex comprising the compound of claim 7 and $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$.

25. A complex comprising the compound of claim 8 and $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$.

26. A complex comprising the compound of claim 9 and $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$.

27. A complex comprising the compound of claim 10 and $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$.

28. A complex comprising the compound of claim 11 and $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$.

29. A complex comprising the compound of claim 12 and $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$.

30. A complex comprising the compound of claim 13 and $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$.

31. A complex comprising the compound of claim 14 and $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$.

32. A complex comprising the compound of claim 15 and $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$.

33. A complex comprising the compound of claim 16 and $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$.

34. A complex comprising the compound of claim 17 and $^{99m}Tc(V)0$, $Re(V)0$, $In^{+3}$, $^{67}Ga^{+3}$, $^{90}Y^{+3}$, $^{109}Pd^{+2}$ or $^{105}Rh^{+3}$.

35. A composition comprising a diagnostic imaging amount of at least one complex as claimed in claim 18, and a pharmaceutically acceptable carrier therefor.

36. The composition of claim 35, wherein the complex contains $^{99m}Tc(V)0$.

37. A composition comprising a diagnostic imaging amount of at least one complex as claimed in claim 33, and a pharmaceutically acceptable carrier therefor.

38. The composition of claim 37, wherein the complex contains $^{99m}Tc(V)0$.

39. A composition comprising a diagnostic imaging amount of at least one complex as claimed in claim 34, and a pharmaceutically acceptable carrier therefor.

40. The composition of claim 39, wherein the complex contains $^{99m}Tc(V)0$.

41. A composition comprising a radiotherapeutic amount of at least one complex as claimed in claim 18, and a pharmaceutically acceptable carrier therefor, wherein the complex includes $Re(V)0$, $In^{+3}$, $^{67}Ga^{+3}$, $^{90}Y^{+3}$, $^{109}Pd^{+2}$ or $^{105}Rh^{+3}$.

42. A composition comprising a radiotherapeutic amount of at least one complex as claimed in claim 33, and a pharmaceutically acceptable carrier therefor, wherein the complex includes $Re(V)0$, $In^{+3}$, $^{67}Ga^{+3}$, $^{90}Y^{+3}$, $^{109}Pd^{+2}$ or $^{105}Rh^{+3}$.

43. A composition comprising a radiotherapeutic amount of at least one complex as claimed in claim 34, and a pharmaceutically acceptable carrier therefor, wherein the complex includes $Re(V)0$, $In^{+3}$, $^{67}Ga^{+3}$, $^{90}Y^{+3}$, $^{109}Pd^{+2}$ or $^{105}Rh^{+3}$.

44. A compound for use in radioimaging and radiotherapy, wherein said compound is:

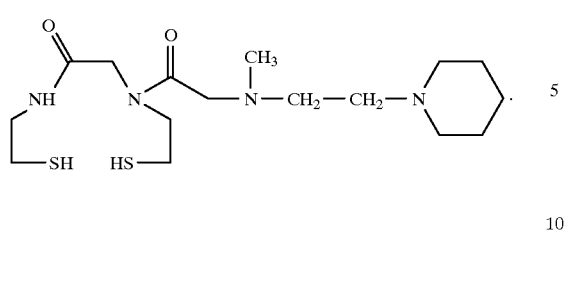
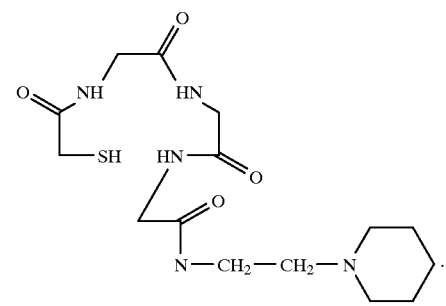
45. A compound for use in radioimaging and radiotherapy, wherein said compound is:
* * * * *

UNITED STATES PATENT AND TRADEMARK OFFICE
CERTIFICATE OF CORRECTION

PATENT NO.: 5,919,934

DATED: July 6, 1999

INVENTOR(S): JOHN et al.

It is certified that an error appears in the above-identified patent and that said Letters Patent is hereby corrected as shown below:

At column 32, line 38 (claim 1), change "wi" to --with at--;

column 32, line 40, change "ca" to --carbon--.

At column 34, lines 26-46 (claim 16), change "●" to -- -- -- as follows:

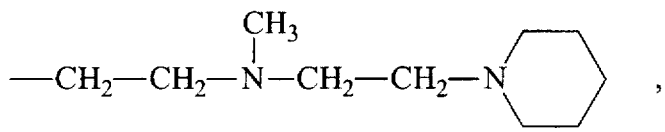

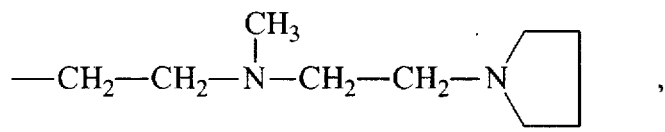

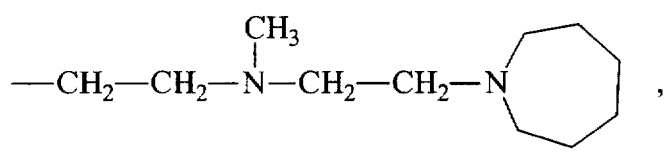

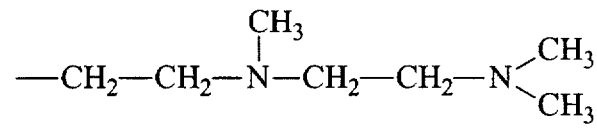

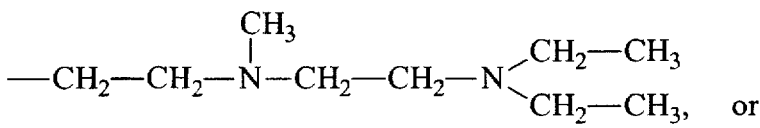

UNITED STATES PATENT AND TRADEMARK OFFICE
CERTIFICATE OF CORRECTION

PATENT NO.: 5,919,934

DATED: July 6, 1999

INVENTOR(S): JOHN et al.

It is certified that an error appears in the above-identified patent and that said Letters Patent is hereby corrected as shown below:

At column 34, line 5 (claim 10), insert an --R-- before "11" in the third formula;

line 5 will read as follows:

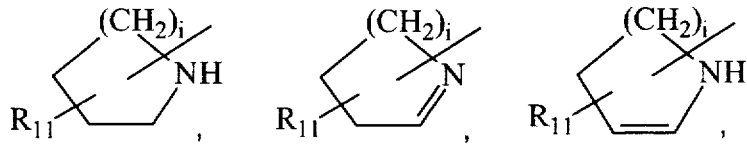

Signed and Sealed this

Twenty-first Day of December, 1999

Attest:

Q. TODD DICKINSON

Attesting Officer

Acting Commissioner of Patents and Trademarks